United States Patent [19]

Faustini et al.

[11] Patent Number: 4,551,476
[45] Date of Patent: Nov. 5, 1985

[54] 13,14-DIDEHYDRO-PROSTAGLANDINS AND PROCESS FOR THEIR PREPARATION

[75] Inventors: Franco Faustini, Milan; Carlo Passarotti, Gallarate; Roberto Ceserani; Carmelo Gandolfi, both of Milan, all of Italy

[73] Assignee: Farmitalia Carlo Erba S.p.A., Milan, Italy

[21] Appl. No.: 493,294

[22] Filed: May 10, 1983

Related U.S. Application Data

[60] Division of Ser. No. 156,813, Jun. 5, 1980, abandoned, which is a continuation of Ser. No. 69,378, Aug. 24, 1979, abandoned, which is a continuation of Ser. No. 952,324, Oct. 18, 1978, abandoned.

[30] Foreign Application Priority Data

Nov. 15, 1977 [IT] Italy .................. 29654 A/77

[51] Int. Cl.$^4$ .................. A61K 177/00; C07D 307/46
[52] U.S. Cl. .................. 514/461; 514/471; 546/283; 548/356; 548/374; 548/379; 549/496; 549/501
[58] Field of Search .............. 549/501, 496; 548/379, 548/374, 356; 546/283; 424/285

[56] References Cited

U.S. PATENT DOCUMENTS 4,035,415 7/1977 Gandolfi .................. 562/503

Primary Examiner—Robert Gerstl
Attorney, Agent, or Firm—Murray, Whisenhunt and Ferguson

[57] ABSTRACT

Omega furyl prostenynoic acids have been prepared.

18 Claims, No Drawings

13,14-DIDEHYDRO-PROSTAGLANDINS AND PROCESS FOR THEIR PREPARATION

This is a divisional application of Ser. No. 156,813, filed June 5, 1980, now abandoned, which is a continuation of Ser. No. 69,378, filed Aug. 24, 1979, now abandoned, which is a continuation of Ser. No. 952,324, filed Oct. 18, 1978, now abandoned.

This invention concerns new 13,14-didehydroprostaglandins a method for their preparation and pharmaceutical and veterinary compositions containing them.

The compounds covered by this invention are optically active or racemic prostaglandin derivatives of formula (I)

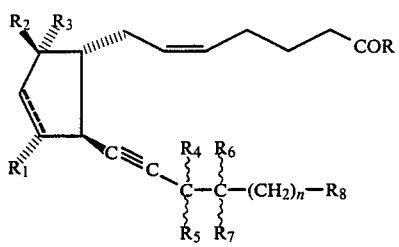

where R is OH; $C_1-C_{12}$ alkoxy with optional substitution by one or more aromatic or heterocyclic radicals; or a

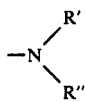

group where R' and R" are, independently of one another, hydrogen, $C_1-C_6$ alkyl, aryl or heterocyclic, or a heterocyclic radical formed by R', R" and the nitrogen; the symbol ----- represents a single or double bond, where, when ----- is a double bond, $R_1$ is hydrogen and $R_2$ and $R_3$, taken together, form an oxo group, and when ----- is a single bond, $R_1$ is hydroxy, $R_2$ is hydrogen and $R_3$ is either hydroxy or acyloxy or forms with $R_2$ an oxo group; one of $R_4$ and $R_5$ is hydroxy or $C_1-C_6$ alkoxy and the other is hydrogen, $C_1-C_4$ alkyl, phenyl, $C_2-C_4$ alkenyl or $C_2-C_4$ alkynyl; $R_6$ and $R_7$ are, independently of one another, hydrogen, $C_1-C_4$ alkyl, fluoro, phenyl or substituted phenyl; n is zero, 1, 2 or 3; $R_8$ is (a) a heterocyclic ring containing at least one double bond and at least one heteroatom chosen from N, S and O, unsubstituted or substituted with one or more substituents chosen from a group consisting of (a') halogen, (b') trihalo-$C_1-C_6$-alkyl, (c') $C_1-C_4$ alkyl, (d') $C_1-C_4$ alkoxy, (e') phenyl and (f') phenoxy; (b) a saturated heterocyclic ring containing at least two heteroatoms chosen from N, S and O, unsubstituted or substituted with one or more substituents (a'), (b') (c'), (d'), (e') and (f') above; (c) a cycloalkenyl group, unsubstituted or substituted with one or more substituents (a'), (b'), (c'), (d'), (e') and (f') above; (d) a monocycloalkyl, bicycloalkyl or tricycloalkyl group, unsubstituted or substituted with one or more of substituents (a'), (b'), (c'), (d'), (e') and (f') above; (e) a saturated heterocyclic ring containing only one heteroatom chosen from N, S and O, unsubstituted or substituted with one or more substituents (a'), (b'), (c'), (d'), (e') and (f') above; with the condition that $R_8$ is (1) an unsubstituted saturated heterocyclic ring containing only one heteroatom or (2) a saturated heterocyclic ring containing only one nitrogen atom and substituted only with a $C_1-C_4$ alkyl group bound to the nitrogen or (3) a cyclohexyl substituted only by a 4-tert-butyl group or $R_8$ is 2-norbornyl, 1-adamantyl, 2-bicyclo[2.2.2]octyl, unsubstituted, exclusively when R is

where R' and R" are as defined above or R is a $C_1-C_{12}$ substituted carbalkoxy and/or at least one of $R_4$ and $R_5$ is $C_1-C_6$ alkoxy, $C_1-C_4$ alkyl, phenyl, $C_2-C_4$ alkenyl or $C_2-C_4$ alkynyl and/or at least one of $R_6$ and $R_7$ is fluorine or optionally substituted phenyl, and with the final condition that $R_8$ is an unsubstituted monocycloalkyl group exclusively when R is

where R' and R" are as described above, or R is a substituted $C_1-C_{12}$ carbalkoxy and/or at least one of $R_4$ and $R_5$ is $C_1-C_6$ alkoxy, $C_1-C_4$ alkyl, phenyl, $C_2-C_4$ alkenyl, $C_2-C_4$ alkynyl and/or at least one of $R_6$ and $R_7$ is optionally substituted phenyl, as well as their pharmaceutically or veterinarily acceptable salts with acids or bases.

The formula reported above for the compounds covered by this invention includes all possible isomers, in particular, steroisomers as well as their mixtures, for example mixtures of diastereoisomers. The double bond is 5(6) is a cis double bond. In the formulas in this invention, dashed lines (ıııı) indicate that the substituents are in the α configuration, that is, beneath the plane of the ring or, for substituents on a side chain, in the (S) configuration. Wedges (—) indicate that the substituents are in the β configuration, that is, above the plane of the ring, or for substituents on a side chain, in the (R) configuration. Wavy lines ( ξ ) indicate that the groups, when the carbon atom to which they are bound is asymmetric, may be both in the α configuration —or (S)—and in the β—or (R)—, as well as in a mixture of the two diastereomers. For example, the hydroxy or $C_1-C_6$ alkoxy group bound to the carbon atom in position 15 may be in configurations (R), (S) and (S,R), that is, a mixture of the 15S and 15R diastereomers. The situation is analogous for the remaining substituents on the carbon atom in position 15. In the same way, when the carbon atom in position 16 has two different substituents, these may be 16S, 16R and 16S,R, that is a mixture of the two 16S and 16R diastereomers.

Of course, when the symbol ----- represents a double bond and so $R_3$ is a hydrogen atom bound to a carbon which is no longer asymmetric, this hydrogen atom is in the plane of the ring and so neither in the α nor β configuration (that is, neither below nor above the ring).

The alkyl, alkoxy, alkenyl, alkynyl and trihaloalkyl groups can be straight or branched chains. When R is a $C_1-C_{12}$ alkoxy group, ethoxy, methoxy or heptyloxy is preferred. When R is a $C_1-C_{12}$ alkoxy optionally substituted with one or more aromatic radicals, these are preferably phenyl groups optionally substituted with $C_1-C_6$ alkyl or halo-$C_1-C_6$ alkyl, particularly trihalo- $C_1$–$C_6$ alkyl, while the heterocyclic radicals are preferably chosen from the group: pyridyl, pyrazolyl and pyrazolinyl. When R is a

group, and one or both of the R' and R'' groups are heterocycles or when R' and R'' form, with the nitrogen atom, a heterocyclic radical, the heterocycle is preferably chosen from the group: pyridyl, pyrazolyl, pyrazolinyl. When $R_3$ is acyloxy, this is preferably a $C_2$–$C_6$ alkanoyloxy group, for example, acetoxy or propionyloxy, or a benzoyloxy group. When one of $R_4$ and $R_5$ is hydrogen and the other is $C_1$–$C_6$ alkoxy, this is preferably methoxy or ethoxy. When one of $R_4$ and $R_5$ is hydroxy or $C_1$–$C_6$ alkoxy and the other is $C_2$–$C_4$ alkenyl, the alkenyl is preferably vinyl or allyl. When one of $R_4$ and $R_5$ is hydroxy or $C_1$–$C_6$ alkoxy and the other is $C_2$–$C_4$ alkynyl, the alkynyl is preferably ethynyl. When $R_6$ and/or $R_7$ are $C_1$–$C_4$ alkyl, this is preferably methyl or ethyl. An aryl group is preferably phenyl; a trihaloalkyl group, trifluoromethyl. When $R_6$ and/or $R_7$ are substituted phenyl, the phenyl substituents are preferably chosen from the group: methyl, chloro, fluoro, trifluoromethyl. When $R_8$ is a heterocyclic ring containing at least one double bond, optionally substituted as described in point (a) above, this is preferably furyl, thienyl, N-alkylpyrrolyl, pyridyl. When $R_8$ is a saturated heterocyclic ring containing at least two heteroatoms, optionally substituted as described above in point (b), this is preferably tetrahydrothiazolyl, tetrahydropyrazolyl, tetrahydroimidazolyl, optionally N-alkylated. When $R_8$ is a cycloalkyl or cycloalkenyl group, optionally substituted as described above in points (c) and (d), this preferably contains from 3 to 7 carbon atoms and is cyclopentyl, cyclohexyl, cycloheptyl, cyclopentenyl, cyclohexenyl, or cycloheptenyl. When $R_8$ is a saturated heterocyclic ring containing only one heteroatom, optionally substituted as described in point (e) above, this is preferably tetrahydrofuryl, tetrahydropyrrolyl, optionally N-alkylated, tetrahydrothienyl. As stated above, this invention also covers pharmaceutically or veterinarily acceptable salts of these compounds with acids or bases. Examples of particularly preferred salts are those of compounds where R in formula (I) is hydroxy, with both inorganic and organic bases.

Examples of pharmaceutically and veterinarily acceptable bases include the hydroxides of lithium, sodium, potassium, calcium, magnesium, aluminum. Examples of particularly preferable organic bases include methylamine, diethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and similar; aliphatic, cycloaliphatic, aromatic and heterocyclic amines like, for example, piperidine, morpholine, pyrrolidine, piperazine, even if substituted, as in, for example, 1-methylpiperidine, 4-ethylmorpholine, 1-isopropylpyrrolidine, 2-methylpyrrolidine, 1,4-dimethylpiperazine, 2-methylpiperidine; also hydrophilic derivatives like mono-, di-, triethanolamine, 2-amino-1-butanol, 2-amino-2-ethyl-1,3-butylethanolamine, 2-amino-2-ethyl-1,3-propandiol, 2-amino-2-methyl-1-propanol, tris-(hydroxymethyl)-aminomethane, N-phenylethanolamine, N-(p-tert-amylphenyl)-diethanolamine, ephedrine, procaine and other similar compounds.

Additional pharmaceutically or veterinarily acceptable salts of the compounds covered by this invention include those with amino acids like lysine, arginine and others, and those with quaternary ammonium salts like tetramethylammonium, tetraethylammonium, benzyltrimethylammonium, phenyltriethylammonium, trimethylcetylammonium, and so on. Pharmaceutically or veterinarily acceptable acids are both organic (for example, citric, tartaric, fumaric, methanesulfonic and malic acids) and inorganic (for example, hydrochloride, hydrobromide and sulfuric acids).

The nor-compounds are those in which n is 3; the dinor—those in which n is 2; the trinor—those in which n is 1; and the tetranor—those in which n is zero.

Examples of preferred compounds according to this invention are:

9α,11α,15(S)-trihydroxy-18,19,20-trinor-17(2')-furanyl-prost-cis-5-en-13-ynoic acid;

9α,11α,15(S)-trihydroxy-18,19,20-trinor-17(3')-furanyl-prost-cis-5-en-13-ynoic acid;

9α,11α,15(S)-trihydroxy-18,19,20-trinor-16(S)-methyl-17(2')-furanyl-prost-cis-5-en-13-ynoic acid;

9α,11α,15(S)-trihydroxy-18,19,20-trinor-16(R)-methyl-17(2')-furanyl-prost-cis-5-en-13-ynoic acid;

9α,11α,15(S)-trihydroxy-18,19,20-trinor-16(S,R)-methyl-17(2')-furanyl-prost-cis-5-en-13-ynoic acid;

9α,11α,15(S)-trihydroxy-18,19-20-trinor-16-trinor-16-fluoro-27(2')-furanyl-prost-cis-5-en-13-ynoic acid;

9α,11α,15(S)-trihydroxy-18,19,20-trinor-16,16-dimethyl-17(2')-furanyl-prost-cis-5-en-13-ynoic acid;

9α,11α,15(S)-trihydroxy-18,19,20-trinor-16(S)-methyl-17(3')-furanyl-prost-cis-5-en-13-ynoic acid;

9α,11α,15(S)-trihydroxy-18,19,20-trinor-16(R)-methyl-17(3')-furanyl-prost-cis-5-en-13-ynoic acid;

9α,11α,15(S)-trihydroxy-18,19,20-trinor-16(S,R)-methyl-17(3')-furanyl-prost-cis-5-en-13-ynoic acid;

9α,11α,15(S)-trihydroxy-18,19,20-trinor-16-fluoro-17(3')-furanyl-prost-cis-5-en-ynoic acid;

9α,11α,15(S)-trihydroxy-18,19,20-trinor-16,16-dimethyl-17(3')-furanyl-prost-cis-5-en-13-ynoic acid;

9α,11α,15(S)-trihydroxy-18,19,20-trinor-17(3'-methyl)-2'-furanyl-prost-cis-5-en-13-ynoic acid;

9α,11α,15(S)-trihydroxy-18,19,20-trinor-17(5'-methyl)-2'-furanyl-prost-cis-5-en-13-ynoic acid;

9α,11α,15(S)-trihydroxy-18,19,20-trinor-17(2',5',dimethyl)-3'-furanyl-prost-cis-5-en-13-ynoic acid;

9α,11α,15(S)-trihydroxy-18,19,20-trinor-17(4'-methoxy)-2'-furanyl-prost-cis-5-en-13-ynoic acid;

9α,11α,15(S)-trihydroxy-18,19,20-trinor-17-(5'-phenoxy)-2'-furanyl-prost-cis-5-en-13-ynoic acid;

9α,11α,15(S)-trihydroxy-18,19,20-trinor-17-thienyl-prost-cis-5-en-13-ynoic acid;

9α,11α,15(S)-trihydroxy-18,19,20-trinor-15-methyl-17-(2')-furanyl-prost-cis5-en-13-ynoic acid;

9α,11α,15(S)-trihydroxy-18,19,20-trinor-15-vinyl-17(2')-furanyl-prost-cis-5-en-13-ynoic acid;

9α,11α,15(S)-trihydroxy-18,19,20-trinor-15-ethynyl-17(2')-furanyl-prost-cis-5-en-13-ynoic acid;

9α,11α,15(S)-trihydroxy-18,19,20-trinor-15-methyl-17(3')-furanyl-prost-cis-5-en-13-ynoic acid;

9α,11α,15(S)-trihydroxy-18,19,20-trinor-15-vinyl-17(3')-furanyl-prost-cis-5-en-13-ynoic acid;

9α,11α,15(S)-trihydroxy-18,19,20-trinor-15-ethynyl-17(3')-furanyl-prost-cis-5-en-13-ynoic acid;
9α,11α,15(S)-trihydroxy-18,19,20-trinor-15-methyl-17-thienyl-prost-cis-5-en-13-ynoic acid;
9α,11α,15(S)-trihydroxy-18,19,20-trinor-15-vinyl-17-thienyl-prost-cis-5-en-13-ynoic acid;
9α,11α,15(S)-trihydroxy-18,19,20-trinor-15-ethynyl-17-thienyl-prost-cis-5-en-13-ynoic acid;
9α,11α,15(S)-trihydroxy-18,19,20-trinor-15,16(S)-dimethyl-17(2')-furanyl-prost-cis-5-en-13-ynoic acid;
9α,11α,15(S)-trihydroxy-18,19,20-trinor-15,16(S)-dimethyl-17(3')-furanyl-prost-cis-5-en-13-ynoic acid;
9α,11α,15(S)-trihydroxy-18,19,20-trinor-1,51,6(S,R)-dimethyl-17(2')-furanyl-prost-cis-5-en-13-ynoic acid;
9α,11α,15(S)-trihydroxy-18,19,20-trinor-15,16(S,R)-dimethyl-17(3')-furanyl-prost-cis-5-en-13-ynoic acid;
9α,11α,15(S)-trihydroxy-18,19,20-trinor-15-methyl-17(3'-methyl)-2'-furanyl-prost-cis-5-en-13-ynoic acid;
9α,11α,15(S)-trihydroxy-18,19,20-trinor-15-methyl-17(5'-methyl)-2'-furanyl-prost-cis-5-en-13-ynoic acid;
9α,11α,15(S)-trihydroxy-18,19,20-trinor-15-vinyl-17(3'-methyl)-2'-furanyl-prost-cis-5-en-13-ynoic acid;
9α,11α,15(S)-trihydroxy-18,19,20-trinor-15-ethynyl-17-(3'-methyl)-2'-furanyl-prost-cis-5-en-13-ynoic acid;
9α,11α,15(S)-trihydroxy-18,19,20-trinor-15-methyl-17(2',5'-dimethyl)-2'-furanyl-prost-cis-5-en-13-ynoic acid;
9α,11α,15(S)-trihydroxy-18,19,20-trinor-15-vinyl-17(2',5'-dimethyl)-2'-furanyl-prost-cis-5-en-13-ynoic acid;
9α,11α,15(S)-trihydroxy-18,19,20-trinor-15-ethynyl-17(2',5'-dimethyl)-2'-furanyl-prost-cis-5-en-13-ynoic acid;
9α,11α,15(S)-trihydroxy-18,19,20-trinor-15-methyl-17(4'-methoxy)-2'-furanyl-prost-cis-5-en-13-ynoic acid;
9α,11α,15(S)-trihydroxy-18,19,20-trinor-15-vinyl-17(4'-methoxy)-2'-furanyl-prost-cis-5-en-13-ynoic acid;
9α,11α,15(S)-trihydroxy-18,19,20-trinor-15-ethynyl-17(4'-methoxy)-2'-furanyl-prost-cis-5-en-13-ynoic acid; p0 9α,11α,15(S)-trihydroxy-18,19,20-trinor-15-methyl-17(5'-phenoxy)-2'-furanyl-prost-cis-5-en-13-ynoic acid;
9α,11α,15(S)-trihydroxy-18,19,20-trinor-15-vinyl-17(5'-phenoxy)-2'-furanyl-prost-cis-5-en-13-ynoic acid;
9α,11α,15(S)-trihydroxy-18,19,20-trinor-15-ethynyl-17-(5'-phenoxy)-2'-furanyl-prost-cis-5-en-13-ynoic acid;
9α,11α,15(S)-trihydroxy-18,19,20-trinor-15-methyl-17-(2')-norbornyl-prost-cis-5-en-13-ynoic acid;
9α,11α,15(S)-trihydroxy-18,19,20-trinor-15-vinyl-17(2')-norbornyl-prost-cis-5-en-13-ynoic acid;
9α,11α,15(S)-trihydroxy-18,19,20-trinor-15-ethynyl-17(2')-norbornyl-prost-cis-5-en-13-ynoic acid;
9α,11α,15(S)-trihydroxy-18,19,20-trinor-15-methyl-17(1')-adamantyl-prost-cis-5-en-13-ynoic acid;
9α,11α,15(S)-trihydroxy-18,19,20-trinor-15-vinyl-17(1')-adamantyl-prost-cis-5-en-13-ynoic acid;
9α,11α,15(S)-trihydroxy-18,19,20-trinor-15-ethynyl-17(1')-adamantyl-prost-cis-5-en-13-ynoic acid;
9α,11α,15(S)-trihydroxy-18,19,20-trinor-15-methyl-17(2')bicyclo 2,2,2 octyl-prost-cis-5-en-13-ynoic acid;
0α,11α,15(S)-trihydroxy-18,19,20-trinor-15-vinyl-17(2')bicyclo[2,2,2]octyl-prost-cis-5-en-13-ynoic acid;
9α,11α,15(S)-trihydroxy-18,19,20-trinor-15-ethynyl-17(2')bicyclo[2,2,2 octyl]prost-cis-5-en-13-ynoic acid;
9α,11α,15(S)-trihydroxy-18,19,20-trinor-15-methyl-17-cyclohexyl-prost-cis-5-en-13-ynoic acid;
9α,11α,15(S)-trihydroxy-18,19,20-trinor-15-vinyl-17-cyclohexyl-prost-cis-5-en-13-ynoic acid;
9α,11α,15(S)-trihydroxy-18,19,20-trinor-15-ethynyl-17-cyclohexyl-prost-cis-5-en-13-ynoic acid;
9α,11α,15(S)-trihydroxy-18,19,20-trinor-15-methyl-17-cycloheptyl-prost-cis-5-en-13-ynoic acid;
9α,11α,15(S)-trihydroxy-18,19,20-trinor-15-vinyl-17-cycloheptyl-prost-cis-5-en-13-ynoic acid;
9α,11α,15(S)-trihydroxy-18,19,20-trinor-15-ethynyl-17-xcycloheptyl-prost-cis-5-en-13-ynoic acid;
9α,11α,15(S)-trihydroxy-18,19,20-trinor-15-methyl-17-cyclopentyl-prost-cis-5-en-13-ynoic acid;
9α,11α,15(S)-trihydroxy-18,19,20-trinor-15-vinyl-17-cyclopentyl-prost-cis-5-en-13-ynoic acid;
9α,11α,15(S)-trihydroxy-18,19,20-trinor-15-ethynyl-17-cyclopentyl-prost-cis-5-en-13-ynoic acid;
9α,11α,15(S)-trihydroxy-18,19,20-trinor-15-methyl-17-cyclopropyl-prost-cis-5-en-13-ynoic acid;
9α,11α,15(S)-trihydroxy-18,19,20-trinor-15-vinyl-17-cyclopropyl-prost-cis-5-en-13-ynoic acid;
9α,11α,15(S)-trihydroxy-18,19,20-trinor-15-ethynyl-17-cyclopropyl-prost-cis-5-en-13-ynoic acid;
9α,11α,15(S)-trihydroxy-18,19,20-trinor-15-methyl-17-cyclohexyl-(4'-phenyl)-prost-cis-5-en-13-ynoic acid;
9α,11α,15(S)-trihydroxy-18,19,20-trinor-15-methyl-17-(4'-tertbutyl-cyclohexyl)-prost-cis-5-en-13-ynoic acid;
9α,11α,15(S)-trihydroxy-18,19,20-trinor-17-cyclopent-2'-enyl-prost-cis-5-en-13-ynoic acid;
9α,11α,15(S)-trihydroxy-18,19,20-trinor-17-cyclopent-1'-enyl-prost-cis-5-en-13-ynoic acid;
9α,11α,15(S)-trihydroxy-18,19,20-trinor-16(S,R)-methyl-17-cyclopent-1'enyl-prost-cis-5-en-13-ynoic acid;
9α,11α,15(S)-trihydroxy-18,19,20-trinor-16(S,R)-methyl-17-cyclopent-2'-enyl-prost-cis-5-en-13-ynoic acid;
0α,11α,15(S)-trihydroxy-18,19,20-trinor-16,16-dimethyl-17-cyclopent-2'-enyl-prost-cis-5-en-13-ynoic acid;
9α,11α,15(S)-trihydroxy-18,19,20-trinor-16,16-dimethyl-17-cyclopent-1'-enyl-prost-cis-5-en-13-ynoic acid;
9α,11α,16(S)-trihydroxy-18,19,20-trinor-15-methyl-17-cyclopent-1'-enyl-prost-cis-5-en-13-ynoic acid;
9α,11α,15(S)-trihydroxy-18,19,20-trinor-15-methyl-17-cyclopent-2'-enyl-prost-cis-5-en-13-ynoic acid;
9α,11α,15(S)-trihydroxy-18,19,20-trinor-15-vinyl-17-cyclopent-2'-enyl-prost-cis-5-en-13-ynoic acid;
9α,11α,15(S)-trihydroxy-18,19,20-trinor-15-vinyl-17-cyclopent-1'-enyl-prost-cis-5-en-13-ynoic acid;
9α,11α,15(S)-trihydroxy-18,19,20-trinor-15-ethynyl-17-cyclopent-1'-enyl-prost-cis-5-en-13-ynoic acid;
9α,11α,15(S)-trihydroxy-18,19,20-trinor-15-ethynyl-17-cyclopent-2'-enyl-prost-cis-5-en-13-ynoic acid;
9α,11α,15(S)-trihydroxy-17,18,19,20-tetranor,15,16-dimethyl-16(4'-phenyl)-cyclohexyl-prost-cis-5-en-13-ynoic acid;
9α,11α,15(S)-trihydroxy-17,18,19,20-tetranor-15,16-dimethyl-16(2')furanyl-prost-cis-5-en-13-ynoic acid;
9α,11α,15(S)-trihydroxy-17,18,19,20-tetranor-15,16-dimethyl-16(3')-furanyl-prost-cis-5-en-13-ynoic acid;
9α,11α,15(S)-trihydroxy-17,18,19,20-tetranor-15,16,16-trimethyl-16(2')furanyl-prost-cis-5-en-13-ynoic acid;
9α,11α,15(S)-trihydroxy-17,18,19,20-tetranor-15,16,16-trimethyl-16(3')furanyl-prost-cos-5-en-13-ynoic acid;
9α,11α,15(S)-trihydroxy-17,18,19,20-tetranor-16-phenyl-16-cyclohexyl-prost-cis-5-en-13-ynoic acid;
9α,11α,15(S)-trihydroxy-17,18,19,20-tetranor-16(S)-methyl-16(2')furanyl-prost-cis-5-en-13-ynoic acid;
9α,11α,15(S)-trihydroxy-17,18,19,20-tetranor-16(S)-methyl-16(3')-furanyl-prost-cis-5-en-13-ynoic acid;

9α,11α,15(S)-trihydroxy-17,18,19,20-tetranor-16,16-dimethyl-16(2')-furanyl-prost-cis-5-en-13-ynoic acid;
9α,11α,15(S)-trihydroxy-17,18,19,20-tetranor-16,16-dimethyl-16(3')furanyl-prost-cis-5-en-13-ynoic acid;
9α,11α,15(S)-trihydroxy-19,20-dinor-18(2')furanyl-prost-cis-5-en-13-ynoic acid;
9α,11α,15(S)-trihydroxy-19,20-dinor-18(3')furanyl-prost-cis-5-en-13-noic acid;
9α,11α,15(S)-trihydroxy-19,20-dinor-16(S)-methyl-18(2')furanyl-prost-cis-5-en-13-ynoic acid;
9α,11α,15(S)-trihydroxy-19,20-dinor-16(S)-methyl-18(3')furanyl-prost-cis-5-en-13-ynoic acid;
9-oxo-11α,15(S)-dihydroxy-18,19,20-trinor-17(2')furanyl-prost-cis-5-en-13-ynoic acid;
9-oxo-11α,15(S)-dihydroxy-18,19,20-trinor-17(3')furanyl-prost-cis-5-en-13-ynoic acid;
9-oxo-11α,15(S)-dihydroxy-18,19,20-trinor-16(S)-methyl-17(2')-furanyl-prost-cis-5-en-13-ynoic acid;
9-oxo-11α,15(S)-dihydroxy-18,19,20-trinor-16(R)-methyl-17(2')furanyl-prost-cis-5-en-13-ynoic acid;
9-oxo-11α,15(S)-dihydroxy-18,19,20-trinor-16(S,R)-methyl-17(2')furanyl-prost-cis-5-en-13-ynoic acid;
9-oxo-11α,15(S)-dihydroxy-18,19,20-trinor-16-fluoro-17(2')furanyl-prost-cis-5-en-13-ynoic acid;
9-oxo-11α,15(S)-dihydroxy-18,19,20-trinor-16,16-dimethyl-17(2')fruanyl-prost-cis-5-en-13-ynoic acid;
9-oxo-11α,15(S)-dihydroxy-18,19,20-trinor-16(S)-methyl-17(3')furanyl-prost-cis-5-en-13-ynoic acid;
9-oxo-11α,15(S)-dihydroxy-18,19,20-trinor-16(R)-methyl-17(3')-furanyl-prost-cis-5-en-13-ynoic acid;
9-oxo-11α,15(S)-dihydroxy-18,19,20-trinor-16(S,R)-methyl-17(3')-furanyl-prost-cis-5-en-13-ynoic acid;
9-oxo-11α,15(S)-dihydroxy-18,19,20-trinor-16-fluoro-17(3')furanyl-prost-cis-5-en-13-ynoic acid;
9-oxo-11α,15(S)-dihydroxy-18,19,20-trinor-16,16-dimethyl-17(3')-furanyl-prost-cis-5-en-13-ynoic acid;
9-oxo-11α,15(S)-dihydroxy-18,19,20-trinor-17(3'-methyl)-2'-furanyl-prost-cis-5-en-13-ynoic acid;
9-oxo-11α,15(S)-dihydroxy-18,19,20-trinor-17(5'-methyl)-2'-furanyl-prost-cis-5-en-13-ynoic acid;
9-oxo-11α,16(S)-dihydroxy-18,19,20-trinor-17(2',5'-dimethyl)3'-furanyl-prost-cis-5-en-13-ynoic acid;
9-oxo-11α,15(S)-dihydroxy-18,19,20-trinor-17(4'-methoxy)-2'-furanyl-prost-cis-5-en-13-ynoic acid;
9-oxo-11α,15(S)-dihydroxy-18,19,20-trinor-17(5'-phenoxy)-2'-furanyl-prost-cis-5-en-13-ynoic acid;
9-oxo-11α,15(S)-dihydroxy-18,19,20-trinor-17-thienyl-prost-cis-5-en-13-ynoic acid;
9-oxo-11α,15(S)-dihydroxy-18,19,20-trinor-15-methyl-17(2')furanyl-prost-cis-5-en-13-ynoic acid;
9-oxo-11α,15(S)-dihydroxy-18,19,20-trinor-15-vinyl-17(2')furanyl-prost-cis-5-en-13-ynoic acid;
9-oxo-11α,15(S)-dihydroxy-18,19,20-trinor-15-ethynyl-17(2')furanyl-prost-cis-5-en-13-ynoic acid;
9-oxo-11α,15(S)-dihydroxy-18,19,20-trinor-15-methyl-17(3')furanyl-prost-cis-5-en-13-ynoic acid;
9-oxo-11α,15(S)-dihydroxy-18,19,20-trinor-15-vinyl-17(3')furanyl-prost-cis-5-en-13-ynoic acid;
9-oxo-11α,15(S)-dihydroxy-18,19,20-trinor-15-ethynyl-17(3')-furanyl-prost-cis-5-en-13-ynoic acid;
9-oxo-11α,15(S)-dihydroxy-18,19,20-trinor-15-methyl-17-thienyl-prost-cis-5-en-13-ynoic acid;
9-oxo-11α,15(S)-dihydroxy-18,19,20-trinor-15-vinyl-17-thienyl-prost-cis-5-en-13-ynoic acid;
9-oxo-11α,15(S)-dihydroxy-18,19,20-trinor-15-ethynyl-17-thienyl-prost-cis-5-en-13-ynoic acid;
9-oxo-11α,15(S)-dihydroxy-18,19,20-trinor-15,16(S)-dimethyl-17(2')furanyl-prost-cis-5-en-13-ynoic acid;
9-oxo-11α,15(S)-dihydroxy-18,19,20-trinor-15,16(S)-dimethyl-17(3')-furanyl-prost-cis-5-en-13-ynoic acid;
9-oxo-11α,15(S)-dihydroxy-18,19,20-trinor-15,16(S,R)-dimethyl-17(2')furanyl-prost-cis-5-en-13-ynoic acid;
9-oxo-11α,15(S)-dihydroxy-18,19,20-trinor-15,16(S,R)-dimethyl-17(3')-furanyl-prost-cis-5-en-13-ynoic acid;
9-oxo-11α,15(S)-dihydroxy-18,19,20-trinor-15-methyl-17(3'-methyl)-2'-furanyl-prost-cis-5-e,-13-ynoic acid;
9-oxo-11α,15(S)-dihydroxy-18,19,20-trinor-15-methyl-17(5'-methyl)-2'-furanyl-prost-cis-5-en-13-ynoic acid;
9-oxo-11α,15(S)-dihydroxy-18,19,20-trinor-15-vinyl-17(3'-methyl)-2'-furanyl-prost-cis-5-en-13-ynoic acid;
9-oxo-11α,15(S)-dihydroxy-18,19,20-trinor-15-ethynyl-17(3'-methyl)-2'-furanyl-prost-cis-5-en-13-ynoic acid;
9-oxo-11α,15(S)-dihydroxy-18,19,20-trinor-15-methyl-17(2',5'-dimethyl)-2'-furanyl-prost-cis-5-en-13-ynoic acid;
9-oxo-11α,15(S)-dihydroxy-18,19,20-trinor-15-vinyl-17(2',5'-dimethyl)-2'-furanyl-prost-cis-5-en-13-ynoic acid;
9-oxo-11α,15(S)-dihydroxy-18,19,20-trinor-15-ethynyl-17(2',5'-dimethyl)-2'-furanyl-prost-cis-5-en-13-ynoic acid;
9-oxo-11α,15(S)-dihydroxy-18,19,20-trinor-15-methyl-17(4'-methoxy)-2'-furanyl-prost-cis-5-e,-13-ynoic acid;
9-oxo-11α,15(S)-dihydroxy-18,19,20-trinor-15-vinyl-17(4'-methoxy)-2'-furanyl-prost-cis-5-en-13-ynoic acid;
9-oxo-11α,15(S)-dihydroxy-18,19,20-trinor-15-ethynyl-17(4'-methoxy-2'-furanyl-prost-cis-5-en-13-ynoic acid;
9-oxo-11α,15(S)-dihydroxy-18,19,20-trinor-15-methyl-17(5'-phenoxy)-2'-furanyl-prost-cis-5-en-13-ynoic acid;
9-oxo-11α,15(S)-dihydroxy-18,19,20-trinor-15-vinyl-17(5'-phenoxy)-2'-furanyl-prost-cis-5-en-13-ynoic acid;
9-xox-11α,15(S)-dihydroxy-18,19,20-trinor-15-ethynyl-17(5'-phenoxy)-2'-furanyl-prost-cis-5-en-13-ynoic acid;
9-oxo-11α,15(S)-dihydroxy-18,19,20-trinor-15-methyl-17(2')-norbornyl-prost-cis-5-en-13-ynoic acid;
9-oxo-11α,15(S)-dihydroxy-18,19,20-trinor-15-vinyl-17(2')-norbornyl-prost-cis-5-en-13-ynoic acid;
9-oxo-11α,15(S)-dihydroxy-18,19,20-trinor-15-ethynyl-17(2')-norbornyl-prost-cis-5-en-13-ynoic acid;
9-oxo-11α,15(S)-dihydroxy-18,19,20-trinor-15-methyl-17(1')-adamantyl-prost-cis-5-en-13-ynoic acid;
9-oxo-11α,15(S)-dihydroxy-18,19,20-trinor-15-vinyl-17(1')-adamantyl-prost-cis-5-en-13-ynoic acid;
9-oxo-11α,15(S)-dihydroxy-18,19,20-trinor-15-ethynyl-17(1')-adamantyl-prost-cis-5-en-13-ynoic acid;
9-oxo-11α,15(S)-idhydroxy-18,19,20-trinor-15-methyl-17(2')-bicyclo 2,2,2octyl-prost-cis-5-en-13-ynoic acid;
9-oxo-11α,15(S)-dihydroxy-18,19,20-trinor-15-vinyl-17(2')-bicyclo 2,2,2 octyl-prost-cis-5-en-13-ynoic acid;
9-oxo-11α,15(S)-dihydroxy-18,19,20-trinor-15-ethynyl-17(2')-bicyclo 2,2,2 octyl-prost-cis-5-en-13-ynoic acid;
9-oxo-11α,15(S)-dihydroxy-18,19,20-trinor-15-methyl-17-cyclohexyl-prost-cis-5-en-13-ynoic acid;
9-oxo-11α,15(S)-dihydroxy-18,19,20-trinor-15-vinyl-17-cyclohexyl-prost-cis-5-en-13-ynoic acid;
9-oxo-11α,15(S)-dihydroxy-18,19,20-trinor-15-ethynyl-17-cyclohexyl-prost-cis-5-en-13-ynoic acid;

9-oxo-11α,15(S)-dihydroxy-18,19,20-trinor-15-methyl-17-cycloheptyl-prost-cis-5-en-13-ynoic acid;
9-oxo-11α,15(S)-dihydroxy-18,19,20-trinor-15-vinyl-17-cycloheptyl-prost-cis-5-en-13-ynoic acid;
9-oxo-11α,15(S)-dihydroxy-18,19,20-trinor-15-ethynyl-17-cycloheptyl-prost-cis-5-en-13-ynoic acid;
9-oxo-11α,15(S)-dihydroxy-18,19,20-trinor-15-methyl-17-cyclopentyl-prost-cis-5-en-13-ynoic acid;
9-oxo-11α,15(S)-dihydroxy-18,19,20-trinor-15-vinyl-17-cyclopentyl-prost-cis-5-en-13-ynoic acid;
9-oxo-11α,15(S)-dihydroxy-18,19,20-trinor-15-ethynyl-17-cyclopentyl-prost-cis-5-en-13-ynoic acid;
9-oxo-11α,15(S)-dihydroxy-18,19,20-trinor-15-methyl-17-cyclopropyl-prost-cis-5-en-13-ynoic acid;
9-oxo-11α,15(S)-dihydroxy-18,19,20-trinor-15-vinyl-17-cyclopropyl-prost-cis-5-en-13-ynoic acid;
9-oxo-11α,15(S)-dihydroxy-18,19,20-trinor-15-ethynyl-17-cyclopropyl-prost-cis-5-en-13-ynoic acid;
9-oxo-11α,15(S)-dihydroxy-18,19,20-trinor-15-methyl-17-cyclohexyl-prost-cis-5-en-13-ynoic acid;
9-oxo-11α,15(S)-dihydroxy-18,19,20-trinor-15-methyl-17-(4'-tertbutylcyclohexyl)-prost-cis-5-en-13-ynoic acid;
9-oxo-11α,15(S)-dihydroxy-18,19,20-trinor-17-cyclopent-2'-enyl-prost-cis-5-en-13-ynoic acid;
9-oxo-11α,15(S)-dihydroxy-18,19,20-trinor-17-cyclopent-1'-enyl-prost-cis-5-en-13-ynoic acid;
9-oxo-11α,15(S)-dihydroxy-18,19,20-trinor-16(S,R)-methyl-17-cyclopent-1'-enyl-prost-cis-5-en-13-ynoic acid;
9-oxo-11α,15(S)-dihydroxy-18,19,20-trinor-16(S,R)-methyl-17-cyclopent-2'-enyl-prost-cis-5-en-13-ynoic acid;
9-oxo-11α,15(S)-dihydroxy-18,19,20-trinor-16,16-dimethyl-17-cyclopent-2'-enyl-prost-cis-5-en-13-ynoic acid;
9-oxo-11α,15(S)-dihydroxy-18,19,20-trinor-16,16-dimethyl-17-cyclopent-1'-enyl-prost-cis-5-en-13-ynoic acid;
9-oxo-11α,15(S)-dihydroxy-18,19,20-trinor-15-methyl-17-cyclopent-1'-enyl-prost-cis-5-en-13-ynoic acid;
9-oxo-11α,15(S)-dihydroxy-18,19,20-trinor-15-methyl-17-cyclopent-2'-enyl-prost-cis-5-en-13-ynoic acid;
9-oxo-11α,15(S)-dihydroxy-18,19,20-trinor-15-vinyl-17-cyclopent-2'-enyl-prost-cis-5-en-13-ynoic acid;
9-oxo-11α,15(S)-dihydroxy-18,19,20-trinor-15-vinyl-17-cyclopent-1'-enyl-prost-cis-5-en-13-ynoic acid;
9-oxo-11α,15(S)-dihydroxy-18,19,20-trinor-15-ethynyl-17-cyclopent-1'-enyl-prost-cis-5-en-13-ynoic acid;
9-oxo-11α,15(S)-dihydroxy-18,19,20-trinor-15-ethynyl-17-cyclopent-2'-enyl-prost-cis-5-en-13-ynoic acid;
9-oxo-11α,15(S)-dihydroxy-17,18,19,20-tetranor-15,16-dimethyl-16(4'-phenyl)-cyclohexyl-prost-cis-5-en-13-ynoic acid;
9-oxo-11α,15(S)-dihydroxy-17,18,19,20-tetranor-15,16-dimethyl-16(2')furanyl-prost-cis-5-en-13-ynoic acid;
9-oxo-11α,15(S)-dihydroxt-17,18,19,20-tetranor-15,16-dimethyl-16(3')furanyl-prost-cis-5-en-13-ynoic acid;
9-oxo-11α,15(S)-dihydroxt-17,18,19,20-tetranor-15,16,16-trimethyl-16(2')-furanyl-prost-cis-5-en-13-ynoic acid;
9-oxo-11α,15(S)-dihydroxy-17,18,19,20-tetranor-15,16,16-trimethyl-16(3')-furanyl-prost-cis-5-en-13-ynoic acid;
9-oxo-11α,15(S)-dihydroxt-17,18,19,20-tetranor-16-phenyl-16-cyclohexyl-prost-cis-5-en-13-ynoic acid;
9-oxo-11α,16(S)-dihydroxy-17,18,19,20-tetranor-16(S)-methyl-16(2')-furanyl-prost-cis-5-en-13-ynoic acid;

9-oxo-11α,15(S)-dihydroxt-17,18,19,20-tetranor-16(S)-methyl-16(3')furanyl-prost-cis-5-en-13-ynoic acid;
9-oxo-11α,15(S)-dihydroxy-17,18,19,20-tetranor-16,16-dimethyl-16(2')furanyl-prost-cis-5-en-13-ynoic acid;
9-oxo-11α,15(S)-dihydroxy-17,18,19,20-tetranor-16,16-dimethyl-16(3')furanyl-prost-cis-5-en-13-ynoic acid;
9-oxo-11α,15(S)-dihydroxy-19,20-dinor-18(2')furanyl-prost-cis-5-en-13-ynoic acid;
9-oxo-11α,15(S)-dihydroxy-19,20-dinor-18(3')-furanyl-prost-cis-5-en-13-ynoic acid;
9-oxo-11α,15(S)-dihydroxy-19,20-dinor-16(S)-methyl-18(2')furanyl-prost-cis-5-en-13-ynoic acid;
9-oxo-11α,15(S)-dihydroxy-19,20-dinor-16(S)-methyl-18(3')furanyl-prost-cis-5-en-13-ynoic acid;
9-oxo-15(S)-hydroxy-18,19,20-trinor-17(2')furanyl-prost-cis-5,10-dien-13-ynoic acid;
9-oxo-15(S)-hydroxy-18,19,20-trinor-17(3')furanyl-prost-cis-5,10-dien-13-ynoic acid;
9-oxo-15(S)-hydroxy-18,19,20-trinor-16(S)-methyl-17(2')-furanyl-prost-cis-5,10-dien-13-ynoic acid;
9-oxo-15(S)-hydroxy-18,19,20-trinor-16(R)-methyl-17(2')-furanyl-prost-cis-5,10-dien-13-ynoic acid;
9-oxo-15(S)-hydroxy-18,19,20-trinor-16(S,R)-methyl-17(2')-furanyl-prost-cis-5,10-dien-13-ynoic acid;
9-oxo-15(S)-hydroxy-18,19,20-trinor-16-fluoro-17(2')-furanyl-prost-cis-5,10-dien-13-ynoic acid;
9-oxo-15(S)-hydroxy-18,19,20-trinor-16,16-dimethyl-17(2')-furanyl-prost-cis-5,10-dien-13-ynoic acid;
9-oxo-15(S)-hydroxy-18,19,20-trinor-16(S)-methyl-17(3')-furanyl-prost-cis-5,10-dien-13-ynoic acid;
9-oxo-15(S)-hydroxy-18,19,20-trinor-16(R)-methyl-17(3')-furanyl-prost-cis-5,10-dien-13-ynoic acid;
9-oxo-15(S)-hydroxy-18,19,20-trinor-16(S,R)-methyl-17(3')-furanyl-prost-cis-5,10-dien-13-ynoic acid;
9-oxo-15(S)-hydroxy-18,19,20-trinor-16-fluoro-17(3')-furanyl-prost-cis-5,10-dien-13-ynoic acid;
9-oxo-15(S)-hydroxy-18,19,20-trinor-16,16-dimethyl-17(3')-furanyl-prost-cis-5,10-dien-13-ynoic acid;
9-oxo-15(S)-hydroxy-18,19,20-trinor-17(3'-methyl)-2'-furanyl-prost-cis-5,10-dien-13-ynoic acid;
9-oxo-15(S)-hydroxy-18,19,20-trinor-17(5'-methyl)-2'-furanyl-prost-cis-5,10-dien-13-ynoic acid;
9-oxo-15(S)-hydroxy-18,19,20-trinor-17-2',5'-dimethyl)-3'-furanyl-prost-cis-5,10-dien-13-ynoic acid;
9-oxo-15(S)-hydroxy-18,19,20-trinor-17-(4'-methoxy)-2'-furanyl-prost-cis-5,10-dien-13-ynoic acid;
9-oxo-15(S)-hydroxy-18,19,20-trinor-17(c3-phenoxy)-2'-furanyl-prost-cis-5,10-dien-13-ynoic acid;
9-oxo-15(S)-hydroxy-18,19,20-trinor-17-thienyl-prost-cis-5,10-dien-13-ynoic acid;
9-oxo-15(S)-hydroxy-18,19,20-trinor-15-methyl-17(2')-furanyl-prost-cis-5,10-dien-13-ynoic acid;
9-oxo-15(S)-hydroxy-18,19,20-trinor-15-vinyl-17(2')-furanyl-prost-cis-5,10-dien-13-ynoic acid;
9-oxo-15(S)-hydroxy-18,19,20-trinor-15-ethynyl-17(2')-furanyl-prost-cis-5,10-dien-13-ynoic acid;
9-oxo-15(S)-hydroxy-18,19,20-trinor-15-methyl-17(3')-furanyl-prost-cis-5,10-dien-13-ynoic acid;
9-oxo-15(S)-hydroxy-18,19,20-trinor-15-vinyl-17(3')-furanyl-prost-cis-5,10-dien-13-ynoic acid;
9-oxo-15(S)-hydroxy-18,19,20-trinor-15-ethynyl-17(3')-furanyl-prost-cis-5,10-dien-13-ynoic acid;
9-oxo-15(S)-hydroxy-18,19,20-trinor-15-methyl-17-thienyl-prost-cis-5,10-dien-13-ynoic acid;
9-oxo-15(S)-hydroxy-18,19,20-trinor-15-vinyl-17-thienyl-prost-cis-5,10-dien-13-ynoic acid;
9-oxo-15(S)-hydroxy-18,19,20-trinor-15-ethynyl-17-thienyl-prost-cis-5,10-dien-13-ynoic acid;

9-oxo-15(S)-hydroxy-18,19,20-trinor-15,16(S)-dimethyl-17(2')-furanyl-prost-cis-5,10-dien-13-ynoic acid;
9-oxo-15(S)-hydroxy-18,19,20-trinor-15,16(S)-dimethyl-17(3')-furanyl-prost-cis-5,10-dien-13-ynoic acid;
9-oxo-15(S)-hydroxy-18,19,20-trinor-15,16(S,R)-dimethyl-17(2')-furanyl-prost-cis-5,10-dien-13-ynoic acid;
9-oxo-15(S)-hydroxy-18,19,20-trinor-15,16(S,R)-dimethyl-17(3')-furanyl-prost-cis-5,10-dien-13-ynoic acid;
9-oxo-15(S)-hydroxy-18,19,20-trinor-15-methyl-17(3'-methyl)-2'-furanyl-prost-cis-5,10-dien-13-ynoic acid;
9-oxo-15(S)-hydroxy-18,19,20-trinor-15-methyl-17(5'-methyl)-2'-furanyl-prost-cis-5,10-dien-13-ynoic acid;
9-oxo-15(S)-hydroxy-18,19,20-trinor-15-vinyl-17(3'-methyl-2'-furanyl-prost-cis-5,10-dien-13-ynoic acid;
9-oxo-15(S)-hydroxy-18,19,20-trinor-15-ethynyl-17-(3'-methyl)-2'-furanyl-prost-cis-5,10-dien-13-ynoic acid;
9-oxo-15(S)-hydroxy-18,19,20-trinor-15-methyl-17-(2',5'-dimethyl)-2'-furanyl-prost-cis-5,10-dien-13-ynoic acid;
9-oxo-15(S)-hydroxy-18,19,20-trinor-15-vinyl-17(2',5'-dimethyl)-2'-furanyl-prost-cis-5,10-dien-13-ynoic acid;
9-oxo-15(S)-hydroxy-18,19,20-trinor-15-ethynyl-17-(2',5'-dimethyl)-2'-furanyl-prost-cis-5,10-dien-13-ynoic acid;
9-oxo-15(S)-hydroxy-18,19,20-trinor-15-methyl-17(4'-methoxy)-2'-furanyl-prost-cis-5,10-dien-13-ynoic acid;
9-oxo-15(S)-hydroxy-18,19,20-trinor-15-vinyl-17(4'-methoxy)-2'-furanyl-prost-cis-5,10-dien-13-ynoic acid;
9-oxo-15(S)-hydroxy-18,19,20-trinor-15-ethynyl-17(4'-methoxy)-2'-furanyl-prost-cis-5,10-dien-13-ynoic acid;
9-oxo-15(S)-hydroxy-18,19,20-trinor-15-methyl-17(5'-phenoxy)-2'-furanyl-prost-cis-5,10-dien-13-ynoic acid;
9-oxo-15(S)-hydroxy-18,19,20-trinor-15-vinyl-17(5'-phenoxy)-2'-furanyl-prost-cis-5,10-dien-13-ynoic acid;
9-oxo-15(S)-hydroxy-18,19,20-trinor-15-ethynyl-17(5'-phenoxy)-2'-furanyl-prost-cis-5,10-dien-13-ynoic acid;
9-oxo-15(S)-hydroxy-18,19,20-trinor-15-methyl-17(2')norbornyl-prost-cis-5,10-dien-13-ynoic acid;
9-oxo-15(S)-hydroxy-18,19,20-trinor-15-vinyl-17(2')norbornyl-prost-cis-5,10-dien-13-ynoic acid;
9-oxo-15(S)-hydroxy-18,19,20-trinor-15-ethynyl-17(2')-norbornyl-prost-cis-5,10-dien-13-ynoic acid;
9-oxo-15(S)-hydroxy-18,19,20-trinor-15-methyl-17(1')-adamantyl-prost-cis-5,10-dien-13-ynoic acid;
9-oxo-15(S)-hydroxy-18,19,20-trinor-15-vinyl-17(1')-adamantyl-prost-cis-5,10-dien-13-ynoic acid;
9-oxo-15(S)-hydroxy-18,19,20-trinor-15-ethynyl-17(1')-adamantyl-prost-cis-5,10-dien-13-ynoic acid;
9-oxo-15(S)-hydroxy-18,19,20-trinor-15-methyl-17(2')-bicyclo[2,2,2]octyl-prost-cis-5,10-dien-13-ynoic acid;
9-oxo-15(S)-hydroxy-18,19,20-trinor-15-vinyl-17(2')-bicyclo-[2,2,2]octyl-prost-cis-5,10-dien-13-ynoic acid;
9-oxo-15(S)-hydroxy-18,19,20-trinor-15-ethynyl-17(2')bicyclo-[2,2,2]octyl-prost-cis-5,10-dien-13-ynoic acid;
9-oxo-15(S)-hydroxy-18,19,20-trinor-15-methyl-17-cyclohexyl-prost-cis-5,10-dien-13-ynoic acid;
9-oxo-15(S)-hydroxy-18,19,20-trinor-15-vinyl-17-cyclohexyl-prost-cis-5,10-dien-13-ynoic acid;
9-oxo-15(S)-hydroxy-18,19,20-trinor-15-ethynyl-17-cyclohexyl-prost-cis-5,10-dien-13-ynoic acid;
9-oxo-15(S)-hydroxy-18,19,20-trinor-15-methyl-17-cycloheptyl-prost-cis-5,10-dien-13-ynoic acid;
9-oxo-15(S)-hydroxy-18,19,20-trinor-15-vinyl-17-cycloheptyl-prost-cis-5,10-dien-13-ynoic acid;
9-oxo-15(S)-hydroxy-18,19,20-trinor-15-ethynyl-17-cycloheptyl-prost-cis-5,10-dien-13-ynoic acid;
9-oxo-15(S)-hydroxy-18,19,20-trinor-15-methyl-17-cyclopentyl-prost-cis-5,10-dien-13-ynoic acid;
9-oxo-15(S)-hydroxy-18,19,20-trinor-15-vinyl-17-cyclopentyl-prost-cis-5,10-dien-13-ynoic acid;
9-oxo-15(S)-hydroxy-18,19,20-trinor-15-ethynyl-17-cyclopentyl-prost-cis-5,10-dien-13-ynoic acid;
9-oxo-15(S)-hydroxy-18,19,20-trinor-15-methyl-17-cyclopropyl-prost-cis-5,10-dien-13-ynoic acid;
9-oxo-15(S)-hydroxy-18,19,20-trinor-15-vinyl-17-cyclopropyl-prost-cis-5,10-dien-13-ynoic acid;
9-oxo-15(S)-hydroxy-18,19,20-trinor-15-ethynyl-17-cyclopropyl-prost-cis-5,10-dien-13-ynoic acid;
9-oxo-15(S)-hydroxy-18,19,20-trinor-15-methyl-17-cyclohexyl(4'-phenyl)-prost-cis-5,10-dien-13-ynoic acid;
9-oxo-15(S)-hydroxy-18,19,20-trinor-15-methyl-17-(4'-tert-butylcyclohexyl)-prost-cis-5,10-dien-13-ynoic acid;
9-oxo-15(S)-hydroxy-18,19,20-trinor-17-cyclopent-2'-enyl-prost-cis-5,10-dien-13-ynoic acid;
9-oxo-15(S)-hydroxy-18,19,20-trinor-17-cyclopent-2'-enyl-prost-cis-5,10-dien-13-ynoic acid;
9-oxo-15(S)-hydroxy-18,19,20-trinor-16(S,R)-methyl-17-cyclopent-1'-enyl-prost-cis-5,10-dien-13-ynoic acid;
9-oxo-15(S)-hydroxy-18,19,20-trinor-16(S,R)-methyl-17-cyclopent-2'-enyl-prost-cis-5,10-dien-13-ynoic acid;
9-oxo-15(S)-hydroxy-18,19,20-trinor-16,16-dimethyl-17-cyclopent-2'-enyl-prost-cis-5,10-dien-13-ynoic acid;
9-oxo-15(S)-hydroxy-18,19,20-trinor-16,16-dimethyl-17-cyclopent-1'-enyl-prost-cis-5,10-dien-13-ynoic acid;
9-oxo-15(S)-hydroxy-18,19,20-trinor-15-methyl-17-cyclopent-1'-enyl-prost-cis-5,10-dien-13-ynoic acid;
9-oxo-15(S)-hydroxy-18,19,20-trinor-15-methyl-17-cyclopent-2'-enyl-prost-cis-5,10-dien-13-ynoic acid;
9-oxo-15(S)-hydroxy-18,19,20-trinor-15-vinyl-17-cyclopent-2'-enyl-prost-cis-5,10-dien-13-ynoic acid;
9-oxo-15(S)-hydroxy-18,19,20-trinor-15-vinyl-17-cyclopent-1'-enyl-prost-cis-5,10-dien-13-ynoic acid;
9-oxo-15(S)-hydroxy-18,19,20-trinor-15-ethynyl-17-cyclopent-1'-enyl-prost-cis-5,10-dien-13-ynoic acid;
9-oxo-15(S)-hydroxy-18,19,20-trinor-15-ethynyl-17-cyclopent-2'-enyl-prost-cis-5,10-dien-13-ynoic acid;
9-oxo-15(S)-hydroxy-17,18,19,20-tetranor-15,16-dimethyl-16(4'-phenyl)-cyclohexyl-prost-cis-5,10-dien-13-ynoic acid;
9-oxo-15(S)-hydroxy-17,18,19,20-tetranor-15,16-dimethyl-16(2')furanyl-prost-cis-5,10-dien-13-ynoic acid;
9-oxo-15(S)-hydroxy-17,18,19,20-tetranor-15,16-dimethyl-16(3')furanyl-prost-cis-5,10-dien-13-ynoic acid;
9-oxo-15(S)-hydroxy-17,18,19,20-tetranor-15,16,16-trimethyl-16(2')furanyl-prost-cis-5,10-dien-13-ynoic acid;

9-oxo-15(S)-hydroxy-17,18,19,20-tetranor-15,16,16-trimethyl-16(3')furanyl-prost-cis-5,10-dien-13-ynoic acid;

9-oxo-15(S)-hydroxy-17,18,19,20-tetranor-16-phenyl-16-cyclohexyl-prost-cis-5,10-dien-13-ynoic acid;

9-oxo-15(S)-hydroxy-17,18,19,20-tetranor-16(S)-methyl-16(2')furanyl-prost-cis-5,10-dien-13-ynoic acid;

9-oxo-15(S)-hydroxy-17,18,19,20-tetranor-16(S)-methyl-16(3')furanyl-prost-cis-5,10-dien-13-ynoic acid;

9-oxo-15(S)-hydroxy-17,18,19,20-tetranor-16,16-dimethyl-16(2')furanyl-prost-cis-5,10-dien-13-ynoic acid;

9-oxo-15(S)-hydroxy-17,18,19,20-tetranor-16,16-dimethyl-16(3')furanyl-prost-cis-5,10-dien-13-ynoic acid;

9-oxo-15(S)-hydroxy-19,20-dinor-18(2')furanyl-prost-cis-5,10-dien-13-ynoic acid;

9-oxo-15(S)-hydroxy-19,20-dinor-18(3')furanyl-prost-cis-5,10-dien-13-ynoic acid;

9-oxo-15(S)-hydroxy-19,20-dinor-16(S)-methyl-18(2')furanyl-prost-cis-5,10-dien-13-ynoic acid;

9-oxo-15(S)-hydroxy-19,20-dinor-16(S)-methyl-18(3')furanyl-prost-cis-5,10-dien-13-ynoic acid;

as well as their alkyl esters or amides or pharmaceutically or veterinarily acceptable salts.

Compounds of general formula (I) can be prepared by reaction of a compound of formula (II)

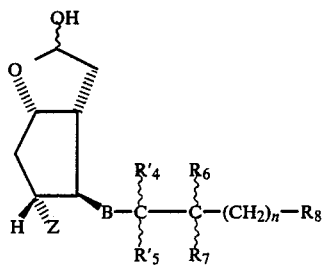
(II)

in optically active or racemic form, where B is C≡C or

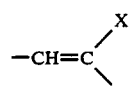

and X is bromo, chloro, or iodo; where $R_6$, $R_7$, $R_8$ and n are as described above; where one of $R_4'$ and $R_5'$ is hydroxyl, $C_1-C_6$ alkoxy or protecting group bound to the chain through an ether linkage and the other is hydrogen, $C_1-C_4$ alkyl, phenyl, $C_2-C_4$ alkenyl, or $C_2-C_4$ alkynyl; and where Z is hydroxyl or a protecting group bound to the ring through an ether linkage, with a Wittig reagent containing a —$(CH_2)_4$—R''' group, where R''' is chosen from (a'') —$CH_2$—$R_9$, where $R_9$ is hydroxy or a protecting group bound to —$CH_2$— through an ether linkage, (b'') —$COOR_{10}$, where $R_{10}$ is hydrogen or $C_1-C_{12}$ alkyl, optionally substituted, (c'')

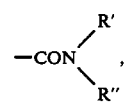

where R' and R'' are described above, to give a compound with formula (III), where the various substituents

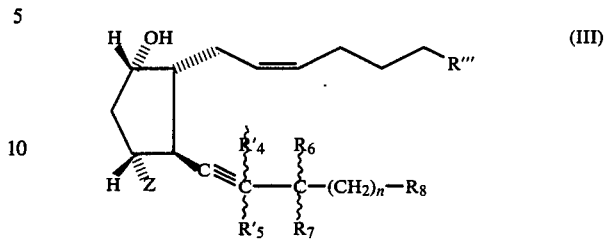
(III)

are as previously reported, which, optionally may be esterified to give the 9α-acyloxy derivative of the compound (III) and/or the protecting groups may be removed or, if desired, it may be oxidized to give a compound with formula (IV),

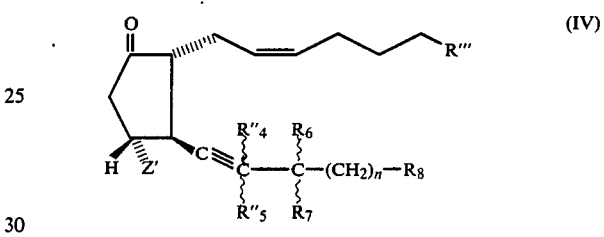
(IV)

where R''', $R_6$, $R_7$, $R_8$ and n are as described above; Z' is a known protecting group as defined above; and one of $R_4''$ and $R_5''$ is a $C_1-C_6$ alkoxy or a known protecting group and the other is hydrogen, $C_1-C_4$ alkyl, phenyl, $C_2-C_4$ alkenyl or $C_2-C_4$ alkynyl, and the protecting groups may be removed to give, depending on the reaction conditions, either a compound (I) where —— is a single bond, $R_1$ is hydroxyl, and $R_2$ and $R_3$ together form an oxo group, or a compound (I) where —— is a double bond, $R_1$ is hydrogen, and $R_2$ and $R_3$ together form an oxo group.

Compounds of formula (III) in which R''' is a —$COOR_{10}$ group where $R_{10}$ is hydrogen may react with a base to give compounds in which R''' is a —COOCat group, where Cat is an inorganic or organic, amine-derived, cation, may be esterified to give compounds in which R''' is a —$COOR_{10}$ group where $R_{10}$ is an optionally substituted $C_1-C_{12}$ alkyl, or may react to form the amide derivative of formula (I) in which R''' is

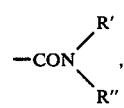

where R' and R'' are as described above.

The protecting groups, for instance, ether groups, are converted to hydroxyl under mild reaction conditions, for example acid hydrolysis. The following groups are examples: 1-alkoxy-cycloalkoxy, 2-oxa-cycloalkyloxy, in which the cycloalkyl ring may optionally contain an oxygen atom, ethers, 1-alkoxy-alkoxy and silylethers. Those preferred are:

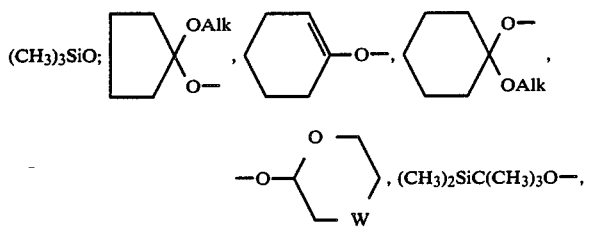

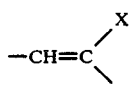

where W is —O— or —CH$_2$— and Alk is a small, e.g. C$_1$-C$_6$, alkyl group.

When B is the lactol of formula (II) is

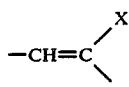

and X is bromo, chloro or iodo, or when B is —C≡C—, the Wittig reaction is complete in 10–20 minutes using from 2 to 5 moles of Wittig reagent per mole of lactol.

When B is the lactol of formula (II) is

—CH=C$\diagup$X$\diagdown$ and X is bromo, chloro or iodo, the hydrogen and halogen are preferably trans to one another.

The Wittig reaction is run under conditions generally employed for this type of reaction; for instance, it is run in an organic solvent like ethyl ether, hexane, dimethylsulfoxide, tetrahydrofuran, dimethylformamide, or hexamethylphosphoramide, in the presence of base, preferably sodium hydride or potassium tert-butylate, at temperatures varying from 0° C. to reflux, but preferably at room temperature.

The term "Wittig reagent" includes compounds of formula (R$_a$)$_3$—P$^{(+)}$—(CH$_2$)$_4$—R''' X'$^{(-)}$, where R$_a$ is aryl or C$_1$-C$_6$alkyl, X' is bromo or chloro, and R''' is as described above. When R$_a$ is alkyl, ethyl is preferred. Preparation of the Wittig reagent is discussed in detail by Trippett, Quart. Rev. 1963, XVII, No. 4406.

For economic reasons, B in the lactol of formula (II) is preferably

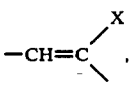

where X is bromo, chloro or iodo, since during the Wittig reaction both the cis and trans derivatives are dehydrohalogenated.

The 9α-hydroxy group in compounds of formula (III) may be optionally acylated by treatment with an anhydride or a carboxylic acid chloride in the presence of base, as in normal organic procedures.

The protecting groups, like ethers, may be removed by hydrolysis with weak acids like mono- or polycarboxylic acids (for instance, formic, acetic, oxalic, citric and tartaric) in a solvent like water, acetone, tetrahydrofuran, 1,2-dimethoxyethane and aliphatic alcohols. Preferably, 0.1N or 0.25N polycarboxylic acid (like oxalic or citric) is used with a low boiling solvent immiscible with water which may be readily removed under vacuum at the end of the reaction.

The oxidation of the 9α-hydroxy group to the oxo derivative may be done with Jones reagent, for example.

As discussed previously, removal of the protecting groups in compounds of formula (IV) may give, depending on the conditions, either a compound of formula (I) where the symbol ____ is a single bond, R is hydroxy and R$_2$ and R$_3$ together form an oxo group, or one in which ____ is a double bond, R is hydrogen and R$_2$ and R$_3$ together form an oxo group. The first may be prepared as the sole reaction product by running the reaction between 25° C. and 35°-38° C., while at higher temperatures, for instance, for several hours at reflux, only the second is obtained.

The lactol of formula (II) can be prepared in a several step process starting from a lactone of formula (V),

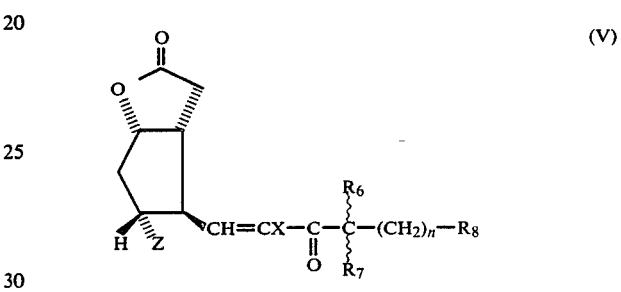

either optically active or racemic, where Z, X, R$_6$, R$_7$ and n are as described above and where the halogen X and the hydrogen bound to the carbon in position 13 may be trans or cis to one another.

The procedure to prepare lactol (II) from lactone (V) involves:

(a''') transformation of lactone (V) to a mixture of 15(S)-ol and 15(R)-ol, (VIa) and (VIb)

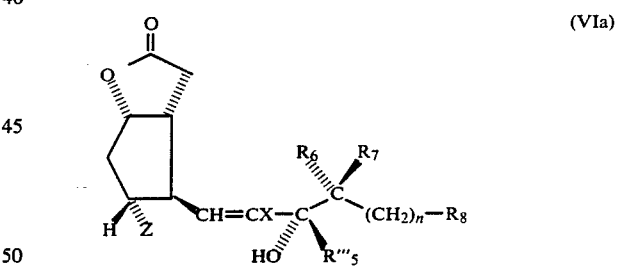

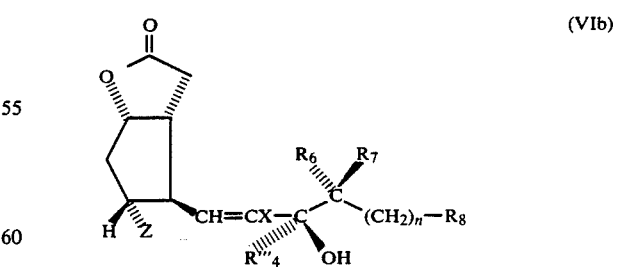

where Z,X,R$_6$,R$_7$,R$_8$ and n are as described above and R$_4$''' and R$_5$''', which are the same, are hydrogen, C$_1$–C$_4$ alkyl, phenyl, C$_2$–C$_4$ alkenyl, C$_2$–C$_4$ alkynyl, followed by the separation of the 15(S)-ol and the 15(R)-ol and, if desired, by the dehydrogalogenation of the separated alcohols to give compounds (VIIa) and (VIIb), where Z, $R_4'''$, $R_5'''$, $R_6$, $R_7$, $R_8$ and n are as described above.

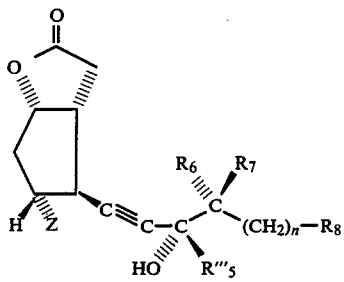
(VIIa)

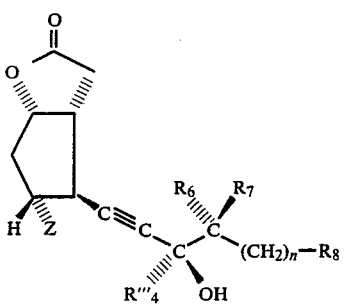
(VIIb)

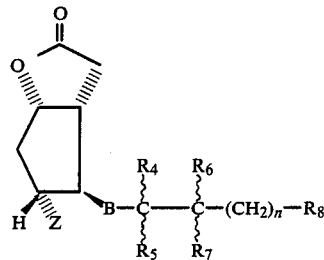
(VIII)

where $Z, B, R_4, R_5, R_6, R_7, R_8$ and n are as described above, into compounds of formula (IX)

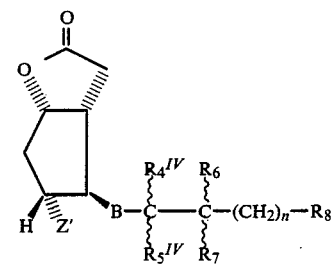
(IX)

where $Z'$, B, $R_6$, $R_7$, $R_8$ and n are as described above, and where one of $R_4^{IV}$ and $R_5^{IV}$ is $C_1$–$C_6$ alkoxy or a protecting group bound to the chain through an ether linkage and the other is hydrogen, $C_1$–$C_4$ alkyl, phenyl, $C_2$–$C_4$ alkenyl, $C_2$–$C_4$ alkynyl.

The optional protection of the free hydroxyl groups by preparing compounds (IX) from compounds (VIII) is done by etherification, preferably with cyclic ethers of formula

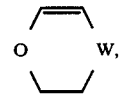

where W is —O— or —CH$_2$—, in the presence of catalytic quantities of compounds like phosphorus oxychloride, or p-toluenesulfonic acid or with halosilanes, for example by reaction with a trialkylchlorosilane in the presence of an acceptor like a trialkylamine, or with 1,1-dialkoxycycloalkanes, for example by reaction with 1,1-dialkoxycyclopentane or -hexane in the presence of an acid catalyst, at reflux in an inert solvent so that the alcohol distills as it is formed.

(c''') reduction of compound (IX) to lactol (X)

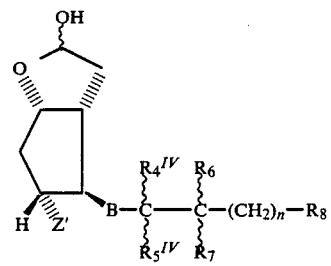
(X)

where $Z', B, R_4^{IV}, R_6, R_7, R_8$ and n are as described above, followed by optional removal of the protecting groups as previously described.

If desired, the dehydrohalogenation may be the first step.

Lactone (V) can readily give a mixture of compounds (VIa) and (VIb) where $R_4'''$ and $R_5'''$ are both hydrogen by reduction in an organic solvent, like acetone, ethyl ether, 1,2-dimethoxyethane, dioxane, benzene or mixtures of these, with a reducing agent like a metal hydride, for example sodium borohydride, lithium borohydride, zinc borohydride, sodium trimethoxyborohydride.

To prepare from lactone (V) a mixture of compounds (VIa) and (VIb) where $R_4'''$ and $R_5'''$, being the same, are $C_1$–$C_4$ alkyl, phenyl, $C_2$–$C_4$ alkenyl, $C_2$–$C_4$ alkynyl, a Grignard reagent like methylmagnesium, ethylmagnesium, phenylmagnesium, vinylmagnesium, or allylmagnesium halide may be used, hydrolyzing the complex formed during the reaction with aqueous ammonium chloride as is commonly done. Alternatively, the reaction may be run with an aluminum alkyl, like trimethylaluminum or triethylaluminum, or with an aromatic or unsaturated aluminum derivative.

The 15(S)-ol may be separated from the epimeric 15(R)-ol by atmospheric or high pressure chromatography or by fractional crystallization. Dehydrohalogenation is effected in a solvent chosen preferably from the group consisting of dimethylsulfoxide, dimethylformamide, hexamethylphosphoramide in the presence of a base which can be an amide of an alkaline metal, an alkaline alcoholate or a methylsulfenylcarbanion.

To prepare the 15(S) and 15(R) alkoxy derivatives from the corresponding 15(S) and 15(R) alcohols, common literature methods may be employed: for instance, reaction with a diazoalkane in the presence of a Lewis acid like borotrifluoroetherate, aluminum chloride or fluoroboric acid (see Fieser et al., *Reagents for Organic Synthesis*, 191, 1967) in an inert solvent like ethyl ether, tetrahydrofuran, benzene or toluene, or reaction with an alkyl halide in the presence of a hydrohalide acid acceptor.

(b''') optional transformation of compounds (VIII)

The reduction is preferably run with diisobutylaluminum hydride or sodium bis-(2-methoxyethoxy)-aluminum hydride in an inert solvent like toluene, n-heptane, n-hexane, benzene or a mixture of them, at temperatures below 30° C.

All compounds prepared according the procedures in points (a'''), (b'''), (c''') may be optically active or racemic.

Lactone (V) may be prepared by the reaction of aldehyde (XI)

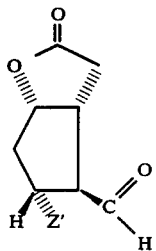

(XI)

where X' is as described above, with a halo-phosphonate carbanion (XI)

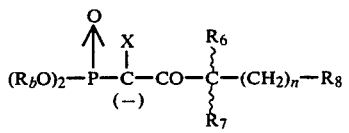

(XII)

followed by optional removal of the protecting groups. In formula (XII) $R_b$ is a small alkyl, e.g. $C_1$-$C_6$ alkyl, and X, $R_6$, $R_7$, $R_8$ and n are as described above.

The reaction of aldehyde (XI) with compound (XII) is readily carried out in an anhydrous solvent, chosen preferably from benzene, 1,2-dimethoxyethane, tetrahydrofuran, dimethylformamide or mixtures of these, with a suspension of 1.1-1.2 molar equivalents of halo-phosphonate carbanion.

Aldehyde (XI) is prepared following literature methods (E. J. Corey et al., Ann. of New York Acad. of Sciences, 180,24(1971)). Halo-phosphonate carbanion XII is prepared by reaction of halo-phosphonate (XIII)

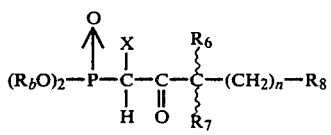

(XIII)

where $R_b$,$R_6$,$R_7$,$R_8$ and n are as described above, with an equivalent amount of base, chosen e.g. from the goup of sodium hydride, lithium hydride, calcium hydride, alkyl lithium derivatives and the $CH_3$—$SO$—$CH_2^-$ anion. Halo-phosphonate (XIII) is prepared by halogenation of phosphonate (XIV)

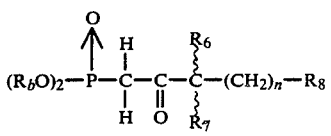

(XIV)

(where $R_b$, $R_6$, $R_7$, $R_8$ and n are as described above) following literature methods, substantially those for the halogenation of β-keto esters.

Phosphonate (XIV) is prepared according to the literature (E. J. Corey et al., J.A.C.S., 90, 3247(1968) and E. J. Corey & G. K. Kwiatowsky, J.A.C.S., 88, 5654(1966)), e.g. preferably by reaction of lithium methylsulfonate with an alkyl ester of a possibly substituted appropriate aliphatic acid. For acids containing asymmetric carbon atoms, both the racemic and the separated optically active forms may be used. These alkyl esters are conveniently prepared following standard procedures: for example, ethyl β-cyclobutylpropionate may be prepared by condensing cyclobutanecarbaldehyde with a phosphonate $(C_2H_5O)_2$—P(→O)—$CH_2$—$COOC_2H_5$, followed by reduction of the product ethyl β-cyclobutylacrylate over Pd/C, for example.

The ethyl esters of the following acids may be prepared from the corresponding esters with a chain of at least two carbon atoms near the carbonyl, by reduction to the alcohol and conversion to the halide followed by the malonic synthesis and subsequent esterification of the product acid: γ-cyclopropylbutyric, α-cyclobutylbutyric, γ-cyclopropylvaleric, γ-cyclohexen(1)propylic, γ-cyclohexan-2-methoxypropylic, γ-furanpropylic, γ-2',5'-dimethylfuranpropylic, γ-2'-phenoxyfuranpropylic.

The esters of substituted propionic acids, like cyclopropane, cyclobutane, cyclopentane, cyclohexane, cycloheptane, 2-tetrahydrofuran, 2-furan, 3-furan, 2-(3-methyl)-furan, 2-(4-methyl)-furan, 2-(5-phenoxy)-furan, cyclopent(1)ene, cyclopent(2)ene, and cyclohexen(3-)ene, derivatives conveniently be prepared from the corresponding substituted acetic acid by common methods: for example, reduction to the primary alcohol, conversion to the mesylate, and halogenation followed by reaction with an appropriate cyanide, like an alkaline metal cyanide, to give nitriles of substituted propionic acids. These may then give the esters by the standard procedures of organic chemistry.

The α-methylation of the above esters by reaction with lithium diisopropylamide in tetrahydrofuran (Org. Syn., 50,58; Tetrahedron Letters,2425,1973) leads to the α-methyl derivatives of the acids reported above, like α-methyl-β-cyclobutylpropionic, α-methyl-β-cyclopropylpropionic, α-methyl-β-cyclobutylpropionic, α-methyl-β-cyclopentylpropionic, α-methyl-β-cyclohexylpropionic, α-methyl-γ-cyclopropylbutyric, α-methyl-γ-cyclobutylbutyric, α-methyl-δ-cyclopropylvaleric, α-methyl-2-tetrahydrofuranylpropionic, α-methyl-2-furanylpropionic, α-methyl-3-furanylpropionic, α-methyl-2-(4-methyl)furanylpropionic, α-methyl-2-(5-methyl)furanylpropionic, α-methyl-2-(5-phenoxy)-furanylpropionic, α-methyl-cyclopent(1)enylpropionic, α-methyl-cyclopent(2)-enylpropionic, α-methyl-cyclohex(3)enylpropionic, as well as other acids mentioned. These may be resolved to give the 2(S) methyl and 2(R) methyl derivatives.

Further methylation of the above esters leads to the α,α-dimethyl derivatives of these acids, like α,α-dimethyl-β-cyclopropylpropionic, α,α-dimethyl-β-cyclopentylpropionic, α,α-dimethyl-β-cyclohexylpropionic, α,α-dimethyl-β-cyclopropylbutyric, α,α-dimethyl-γ-cyclobutylbutyric α,α-dimethyl-δ-cyclopropylvaleric.

Alternatively, a halo-phosphonate carbanion (XII) may be prepared by reaction of a phosphonate carbanion (XIVa)

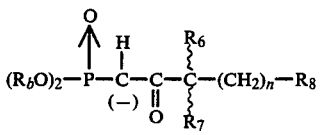

where $R_b$, $R_6$, $R_7$, $R_8$ and n are as described above, with a halogenating agent chosen from the group: bromine, 2-pyrrolidonehydrotribromide (PHTB), dioxane dibromide, N-chloroacetamide, N-chlorosuccinimide, N-bromosuccinimide, N-iodosuccinimide, N-bromocaprolactam. When these imides are used (XII) is prepared directly by using 1 equivalent of base. Otherwise, another equivalent of base is necessary to prepare the halophosphonate carbanion.

Phosphonate carbanion (XIVa) is prepared by treating phosphonate (XIV) with an equivalent of a base like sodium, lithium or calcium hydride.

Halolactone (V) where X is bromine can also be conveniently prepared starting from lactone (XV),

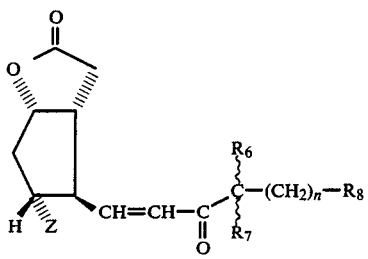

where Z, $R_6$, $R_7$, $R_8$ and n are as described above, which in turn can be prepared using literature methods (E. J. Corey et al., Ann. of New York Acad. of Sciences, 180,24(1971)), in the following series of steps:

($a^{iv}$) halogenation of lactone (XV) to dihalolactone (XVa)

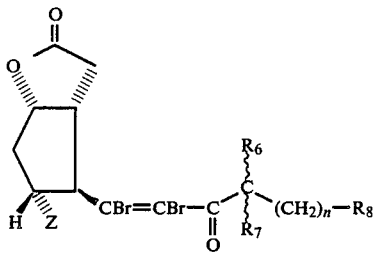

where Z, $R_6$, $R_7$, $R_8$ and n are as described above.

The halogenation is run in an inert solvent, preferably chosen from the group dichloromethane, dichloroethane, carbon tetrachloride, cyclic or open chain ethers like tetrahydrofuran, dioxane, 1,2-dimethoxyethane or mixtures of them, and acetic acid with a molar equivalent or more of halogenating agent chosen from the group bromine, dioxane dibromide, 2-pyrrolidone hydrotribromide;

($b^{iv}$) dehydrohalogenation of dihalolactone (XVa) to give halolactone (XV), where X is bromo. The dehydrohalogenation may be run with an organic base like a tertiary amine or pyridine; either neat or in an inert solvent, or alternatively with an inorganic base like potassium acetate in a suitable solvent, for example, methanol, ethanol, acetic acid.

Steps ($a^{iv}$) and ($b^{iv}$) above can be run together in a suitably-selected solvent to give halolactone (V) directly from lactone (XV). The starting material can be the racemic form of lactone (V) as well as the optically active forms.

In preparing halogenated lactone (V) according to the above methods, the hydrogen and halogen in positions $\beta$ and $\alpha$ to the carbonyl may be either cis or trans to one another depending on the reaction conditions: either the trans is obtained almost exclusively, with a very small quantity of cis, or vice versa. However, under this invention, both the cis and trans isomers may be used to prepare the 13,14-didehydroprostaglandins.

Lactol (II) in which B is —C≡C— may be prepared by dehydrohalogenation of lactol (II) in which B is

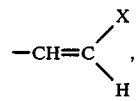

where X is halogen. Dehydrohalogenation may be done in an aprotic solvent preferably chosen from the group dimethylsulfoxide, dimethylformamide and hexamethylphosphoramide by treatment with a base preferably chosen from potassium tert-butylate, an alkaline metal amide and the $CH_3SO-CH_2^{\ominus}$ anion.

Compounds (XVI)

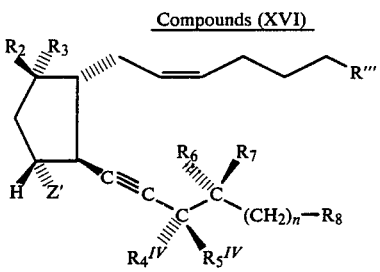

in their optically active or racemic forms where $R'''$, $R_4^{IV}$, $R_5^{IV}$, $R_6$, $R_7$, $R_8$, $Z'$ and n are as described above, where $R_2$ is hydrogen and $R_3$ is a hydroxy or acyloxy group, or where $R_2$ and $R_3$ together form an oxo group are also covered by this invention.

The compounds covered by this invention may be used in all situations where natural prostaglandins are indicated, with the advantages of superior resistance to the enzyme 15-prostaglandin dehydrogenase, which is known to rapidly inactivate natural prostaglandins, and of more selective therapeutic activity.

For example, the compounds of the invention, particularly the 9-hydroxy derivatives, exhibit oxytocic action, that is, they may be substituted for oxytocin to induce labor or to expel a dead fetus in pregnant females, both in humans and in animals. In this application, the compounds are administered either by intravenous infusion at a dose of approximately 0.01 g/kg/minute until the end of labor, or by mouth.

Further, the compounds covered by this invention, particularly the 9-hydroxy derivatives, also show luteolytic activity and so may be used in fertility control with the advantage of a considerably reduced capacity to stimulate the smooth muscles. Therefore, the side effects of natural prostaglandins, like vomiting and diarrhea, are absent.

Another useful pharmacological property of the compounds of this invention, particularly the 9-hydroxy derivatives, is their anti-ulcerogenic activity. In fact, they are useful to reduce and control excessive gastric secretion in mammals, and so reduce or eliminate the formation of gastrointestinal ulcers while accelerating the cure of any ulcers already present in the gastrointestinal tract. In this application, the compounds are administered by intravenous infusion or injection, either subcutaneous or intramuscular. In intravenous infusion, the dose varies from approximately 0.1 μg to 500 μg per kilogram of body weight per minute. The total daily dose, both by injection and by infusion, is on the order of 0.1–20 mg/kg, depending on the patient's or animal's age, weight and condition and on the administration method.

As mentioned above, the compounds covered by this invention may be administered in various ways, according to the application; for instance, they may be given intravenously, intramuscularly, subcutaneously, orally, endovaginally, rectally, topically. In the various pharmaceutical formulations, the excipients and carriers used are conventional: for example, lactose, dextrose, sucrose, mannitol, sorbitol, cellulose, talc, stearic acid, calcium or magnesium stearate, glycols, amides, gum arabic, gum adragant, alginic acid or alginates, lecithin, polysorbates, laurylsulfates, etc., for oral administration. For administration with a vaporizer, a suspension or solution of a compound covered by this invention may be used, preferably as a salt (for instance, of sodium) dissolved in water. Alternatively, the pharmaceutical formulations may be a suspension or solution of a compound under this invention in a common liquified propellant like dichlorofluoromethane or dichlorotetrafluoroethane for administration with a pressurized container, for instance an aerosol. If the compound is not soluble in the propellant, a co-solvent must be added: for example, ethanol, dipropylenic glycol and/or a tensioactive substance to the pharmaceutical formulation. For parenchymal administration, the compound may be dissolved, for example, in sterile water or a lydocain hydrochloride solution, in a dextrose solution or in another solvent commonly used for this type of administration.

This invention is illustrated but not limited by the following examples.

The abbreviations THP, DIOX, DMSO, THF, DMF, DIBA, and Et$_2$O refer to tetrahydropyranyl, dioxanyl, dimethylsulfoxide, tetrahydrofuran, dimethylformamide, diisobutylaluminum hydride and ethyl ether. All temperatures are expressed in degrees centigrade, and optical rotation measures refer to 20° C. and a concentration of 1% by weight of the compound in the specified solvent.

EXAMPLE 1

A solution of 940 mg of dimethyl-[2-oxo-4-(2'-furanyl)]-butylphosphonate in 10 ml of benzene is added dropwise to a suspension of 130 mg of sodium hydride in 25 ml of benzene (80% mineral oil dispersion). The reaction is continued until hydrogen evolution ceases. Then, with stirring, a suspension of 785 mg of N-bromosuccinimide in 10 ml of benzene is added. Stirring is continued for 10 minutes to give the carbanion of dimethyl-[1-bromo-2-oxo-4-(2'-furanyl)]-butylphosphonate. 1.250 g of 2β-formyl-5α-hydroxy-1α-cyclopentanacetic acid-γ-lactone-4α-p-phenylbenzoate is then added and the reaction is continued for 2 hours. The mixture is then diluted with water, and the organic phase is washed successively with water, NaHCO$_3$ and NaH$_2$PO$_4$ solutions, and water. Drying and solvent removal afford a residue which is chromatographed on SiO$_2$ (elution with 95:5 CH$_2$Cl$_2$:Et$_2$O) to give 1.180 g of 3α-p-phenyl-benzoxy-5α-hydroxy-2β-[2-bromo-3-oxo-5-(2'-furan)pent-trans-(1)-enyl]1α-cyclopentane acetic acid-γ-lactone (U.V.λmax 250 mμ; ε=11.500). The mass spectrum shows peaks at 548/550, 469, 271, 198, and 181, NMR (DMSO-d$_6$): doublet 6.8 δ; J$_{AB}$=9.1 H$_z$.

EXAMPLE 2

Under a nitrogen atmosphere, 2.740 g of dimethyl-[2-oxo-4-(2',5'-dimethyl-3'-furan)]-butylphosphonate are added to 337.5 mg of sodium hydride (80% mineral oil dispersion) in 65 ml of anhydrous benzene, until hydrogen evolution ceases. 2 g of 2β-formyl-5α-hydroxycyclopentane acetic acid-4α-benzoxy-γ-lactone is then added and the mixture is stirred until reaction is complete. After dilution with water, the organic phase is washed with saturated monobasic phosphate and water. Solvent removal affords a residue which is chromatographed on SiO$_2$ (elution with 80:20 benzene:Et$_2$O) to give 2.56 g of 3α-benzoxy-5α-hydroxy-2β-[3-oxo-5-(2',5'-dimethyl-3'-furan)pent-trans-1-enyl]-1α-cyclopentane acetic acid-γ-lactone. The mass spectrum shows peaks at 422, 300, 122, and 105.

EXAMPLE 3

528 mg of bromine in 4 ml of glacial acetic acid are added dropwise to a solution of 1.490 g of 3α-benzoxy-5α-hydroxy-2β-[3-oxo-5(2',5'-dimethyl-3'-furan)pent-trans-1-enyl]-1α-cyclopentane acetic acid-γ-lactone in 7 ml of glacial acetic acid. The reaction goes rapidly to completion. The mixture is then heated to 80° C. and 750 mg of potassium carbonate is added. After another two hours at 80° C., the solution is cooled and 100 mg of cold water is added. Filtration affords 1.450 g of 3α-benzoxy-5α-hydroxy-2β-[2-bromo-3-oxo-5-(2',5'-dimethyl-3'-furan)pent-trans-1-enyl]-1α-cyclopentane acetic acid-γ-lactone (U.V.λmax 252 mμ; ε=9.600). The mass spectrum shows peaks at 500/502, 421, 299, 122 and 105;

NMR (DMSO-d$_6$): doublet 6.85 δ; J$_{AB}$=9.15 H$_z$.

EXAMPLE 4

730 mg of dimethyl-2-oxo-3(S)-methyl-4(2')furanbutyl phosphonate are added dropwise to a suspension of 90 mg of sodium hydride (80% mineral oil dispersion) under a nitrogen atmosphere. When the reaction is finished, 554 mg of 2β-formyl-5α-hydroxy-cyclopentane acetic acid-4α-benzoxy-γ-lactone are added and the mixture is stirred until completion. After dilution with water, the organic phase is washed with saturated monobasic phosphate solution and then water until neutral. Solvent removal affords a residue which is chromatographed on SiO$_2$ (elution with 80:20 benzene:Et$_2$O) to give 695 mg of 3α-benzoxy-5α-hydroxy-2β-[3-oxo-4(S)-methyl-5(2')-furanpent-trans-1-enyl]-1α-cyclopentane acetic acid-γ-lactone. The mass spectrum shows peaks at 408, 286, 122 and 105.

EXAMPLE 5

1.354 g of 2-pyrrolidone hydrotribromide is added to a solution of 844 mg of 3α-benzoxy-5α-hydroxy-2β-[3-oxo-4(S)-methyl-5(2')furanpent-trans-1-enyl]-1α-cyclopentane acetic acid-γ-lactone in 20 ml of THF; the resulting mixture is stirred at 25° C. for 15 hours. The completed reaction mixture is diluted with 20 ml of Et₂O, filtered, washed with saturated ammonium sulfate solution and water, and then evaporated to dryness. The crude product is dissolved in 9 ml of pyridine and stirred for 24 hours at 70° C. After dilution with 20 ml of ethyl acetate, the mixture is acidified with 2N H₂SO₄ and then washed with water, NaHCO₃ solution and water. Solvent removal affords a product which is chromatographed on SiO₂ (elution with 1:1 cyclohexane:methylene chloride) to give 795 mg of 3α-benzoxy-5α-hydroxy-2β-[2-bromo-3-oxo-4(S)-methyl-5(2')furanpent-1-trans-enyl]-1α-cyclopentane acetic acid-γ-lactone. The mass spectrum shows peaks at 486/488, 407, 385, 122 and 105;

NMR (DMSO-d₆): doublet 6.80; γ J$_{AB}$=9.2 H$_z$.

EXAMPLE 6

As an alternative to the method of Example 5, 3α-benzoxy-5α-hydroxy-2β-[2-bromo-3-oxo-4(S)-methyl5(2')furanpent-1-trans-enyl]-1α-cyclopentane acetic acid-γ-lactone may be prepared by gradually adding a 3% carbon tetrachloride solution of bromine (48 mg) to a solution of 126.6 mg of 3α-benzoxy-5α-hydroxy-2β-[3-oxo-4(S)-methyl5(2')furanpent-1-trans-enyl]-1α-cyclopentane acetic acid-γ-lactone in 5 ml of methylene chloride. Reaction is complete when a slight red color is seen to persist; 1.25 ml of pyridine is then added and the mixture held at 80° C. for 2 hours. This mixture is then diluted with water, acidified with 4N H₂SO₄, and then separated and extracted with ethyl acetate. The combined extract is evaporated to dryness to give a residue which is chromatographed on SiO₂ (elution with 90:10 cyclohexane:Et₂O) to afford 127.2 mg of the bromoketone mentioned above.

EXAMPLE 7

The following phosphonates may be used as starting materials in the procedure of Example 1 to prepare the respective 3α-acyloxy-5α-hydroxy-2β-[2-bromo-3-oxo-(ω-cycloalkyl-alk-trans-1-enyl)]-1α-cyclopentane acetic acid-γ-lactones, as well as the 2-chloro and 2-iodo derivatives:

dimethyl-(2-oxo-4-cyclopent-1'-enylbutyl)-phosphonate;
dimethyl-(2-oxo-4(3')-furanylbutyl)-phosphonate;
dimethyl-(2-oxo-3(S)-methyl-4(2')furanylbutyl)-phosphonate;
dimethyl-(2-oxo-3(R)-methyl-4(2')furanylbutyl)-phosphonate;
dimethyl-(2-oxo-3(S,R)-methyl-4(2')furanylbutyl)-phosphonate;
dimethyl-(2-oxo-3(S,R)-methyl-4(3')furanylbutyl)-phosphonate;
dimethyl-(2-oxo-3,3-dimethyl-4(2')furanylbutyl)-phosphonate;
dimethyl-(2-oxo-3,3-dimethyl-4(3')furanylbutyl)-phosphonate;
dimethyl-(2-oxo-3,3-dimethyl-4-cyclopent-1'-enylbutyl)-phosphonate;
dimethyl-(2-oxo-3,3-dimethyl-4-cyclopent-2'-enylbutyl)-phosphonate;
dimethyl-(2-oxo-3(S)-methyl-4-cyclopent-2'-enylbutyl)-phosphonate;
dimethyl-(2-oxo-3(R)-methyl-4-cyclopent-2'-enylbutyl)-phosphonate;
dimethyl-(2-oxo-3(S)-methyl-4-cyclopent-1'-enylbutyl)-phosphonate;
dimethyl-(2-oxo-3(R)-methyl-4-cyclopent-1'-enylbutyl)-phosphonate;
dimethyl-(2-oxo-4(3')-methyl-2'-furanylbutyl)-phosphonate;
dimethyl-(2-oxo-4(4')-methyl-2'-furanylbutyl)-phosphonate;
dimethyl-(2-oxo-4(5')-methyl-2'-furanylbutyl)-phosphonate;
dimethyl-(2-oxo-4(2',5')dimethyl-3'-furanylbutyl)-phosphonate;
dimethyl-(2-oxo-4(5')-methoxy-2'-furanylbutyl)-phosphonate;
dimethyl-(2-oxo-4(5')-phenoxy-2'-furanylbutyl)-phosphonate;
dimethyl-2-oxo-3-(3-phenylcyclohexyl)propyl-phosphonate;
dimethyl-2-oxo-4-(2'-thienylbutyl)-phosphonate;
dimethyl-(2-oxo-3(S)-methyl-3(2')furanylpropyl)-phosphonate;
dimethyl-(2-oxo-3,3-dimethyl-3(2')furanylpropyl)-phosphonate.

EXAMPLE 8

The phosphonates listed in example 7 can be used in the procedures reported in examples 2, 3 and 4 to prepare the respective 3α-acyloxy-2β(3-oxo-ω-cycloalkylalk-1-trans-enyl)-1α-cyclopentane acetic acid-γ-lactones. Halogenation to the dihalo derivatives followed by dehydrohalogenation according to the procedures described in examples 5 and 6 lead to the respective 3α-benzoxy-5α-hydroxy-2β-[2-bromo-3-oxo-1-trans-derivatives of:

5-(cyclopent-1'-enyl)-pentenyl]-1α-cyclopentane acetic acid-γ-lactone;
5-(cyclopent-2'-enyl)-pentenyl]-1α-cyclopentane acetic acid-γ-lactone;
5-(2')furanylpentenyl]-1α-cyclopentane acetic acid-γ-lactone;
4(S)-methyl-5(2')-furanylpentenyl]-1α-cyclopentane acetic acid-γ-lactone;
4(R)-methyl-5(2')-furanylpentenyl]-1α-cyclopentane acetic acid-γ-lactone;
4(S,R)-methyl-5(2')furanylpentenyl]-1α-cyclopentane acetic acid-γ-lactone;
4(S,R)-methyl-5(3')-furanylpentenyl]-1α-cyclopentane acetic acid-γ-lactone;
4,4-dimethyl-5(2')-furanylpentenyl]-1α-cyclopentane acetic acid-γ-lactone;
4,4-dimethyl-5(3')-furanylpentenyl]-1α-cyclopentane acetic acid-γ-lactone;
4,4-dimethyl-5-cyclopent-1'-enylpentenyl]-1α-cyclopentane acetic acid-γ-lactone;
4,4-dimethyl-5-cyclopent-2'-enylpentenyl]-1α-cyclopentane acetic acid-γ-lactone;
4(S)-methyl-5-cyclopent-2'-enylpentenyl]-1α-cyclopentane acetic acid-γ-lactone;
4(R)-methyl-5-cyclopent-2'-enylpentenyl]-1α-cyclopentane acetic acid-γ-lactone;
4(S)-methyl-5-cyclopent-1'-enylpentenyl]-1α-cyclopentane acetic acid-γ-lactone;
4(R)-methyl-5-cyclopent-1'-enylpentenyl]-1α-cyclopentane acetic acid-γ-lactone;
5-(3'-methyl-2'-furanylpentenyl)]-1α-cyclopentane acetic acid-γ-lactone;
5-(4'-methyl-2'-furanylpentenyl)]-1α-cyclopentane acetic acid-γ-lactone;
5-(5'-methyl-2'-furanylpentenyl)]-1α-cyclopentane acetic acid-γ-lactone;
5-(2',5'-dimethyl-3'-furanylpentenyl)]-1α-cyclopentane acetic acid-γ-lactone;

5-(4'-methoxy-2'-furanylpentenyl)]-1α-cyclopentane acetic acid-γ-lactone;
5-(5'-phenoxy-2'-furanylpentenyl)]-1α-cyclopentane acetic acid-γ-lactone;
4-(4'-phenyl-cyclohexylpentenyl)]-1α-cyclopentane acetic acid-γ-lactone;
5-(2'-thienylpentenyl)]-1α-cyclopentane acetic acid-γ-lactone;
4-(4(S)-methyl-2'-furanylbutenyl)]-1α-cyclopentane acetic acid-γ-lactone;
4,4-dimethyl-4(2')-furanylbutenyl)]-1α-cyclopentane acetic acid-γ-lactone;
4,4-dimethyl-5(2')furanylpentenyl)]-1α-cyclopentane acetic acid-γ-lactone.

EXAMPLE 9

Following the procedures reported in examples 2, 3 and 4, using the phosphonates listed in example 7, the analogous 3α-p-phenyl-benzoxy and 3α-acetoxy derivatives are prepared.

EXAMPLE 10

2 g of 3α-benzoxy-5α-hydroxy-2β-[2-bromo-3-oxo-4(S)-methyl-5(2')furanylpent-trans-1-enyl]-1α-cyclopentane acetic acid-γ-lactone dissolved in 30 ml of DME are added to 250 ml of a 0.05M zinc borohydride solution, and the mixture is then stirred for another 30 minutes. The solution is diluted by the careful addition of saturated NaCl solution and acidified with 2N H$_2$SO$_4$; the separated organic layer is washed until neutral. Solvent removal gives a residue which is chromatographed on 450 g of silica gel (elution with 1:1 methylene chloride: Et$_2$O) to afford 1.2 g of 3α-benzoxy-5α-hydroxy-2β-[2-bromo-3(S)-hydroxy-4(S)-methyl-5(2')-furanylpent-trans-1-enyl]-1α-cyclopentane acetic acid-γ-lactone and 0.69 g of the epimeric 3(R)-alcohol. The mass spectrum shows peaks at 488/490, 379/381, 269, 122 and 105.

As an alternative to the above procedure, a calcium borohydride solution may be used, prepared by the reaction of sodium borohydride with an anhydrous ether solution of calcium chloride, instead of ethereal zinc borohydride solution as above. The rest of the procedure is identical, giving comparable yields of the 3(S) and 3(R) alcohols.

EXAMPLE 11

2 ml of a 3M solution of methylmagnesium iodide are added to 500 mg of 3α-benzoxy-5α-hydroxy-2β-[2-bromo-3-oxo-5(2')furanylpent-trans-1-enyl]-1α-cyclopentane acetic acid-α-lactone in 5 ml of anhydrous THF cooled to −70° C., in a nitrogenstream. After 10 minutes at −70° C., 1.7 g of NaHSO$_4$ in 3 ml of water is cautiously added. After another 5 minutes, the temperature is allowed to rise to room temperature and the mixture is extracted with ether. The organic extract is washed with saturated ammonium sulfate solution until neutral and then with water. Drying over Na$_2$SO$_4$ and evaporation to dryness give 560 mg of product. Chromatography on silica gel with ethyl ether as eluent affords 200.5 mg of 3α-benzoxy-5α-hydroxy-2β-[2-bromo-3(S)-hydroxy-3-methyl5(2')furanylpent-trans-1-enyl]-1α-cyclopentane acetic acid-γ-lactone and 172.5 mg of the corresponding epimeric 3(R)-alcohol. The mass spectrum shows peaks at 488/490, 393/395, 269, 122 and 105.

Alternatively, the alkylation may be run with, for example, trimethylaluminum in benzene solution at 5° C., under nitrogen; analogous work-up gives the mixture of the epimeric 3(S,R) alcohols, which may in turn be separated into the pure isomers by chromatography on silica gel.

EXAMPLE 12

15 ml of a 10% ethyl ether solution of diazomethane and 3 ml of a 1% methylene chloride solution of boron trifluoride are added to a cooled (−70° C.) solution of 600 mg of 3α-benzoxy-5α-hydroxy-2β-[2-bromo-3(S)-hydroxy-5(2')-furanylpent-trans-1-enyl]-1α-cyclopentane acetic acid-γ-lactone in 6 ml of methylene chloride. After 10 minutes, the mixture is slowly brought to room temperature. Evaporation to dryness under reduced pressure gives 608 mg of 3α-benzoxy-5α-hydroxy-2β-[2-bromo-3(S)-methoxy-5(2')furanylpent-trans-1-enyl]-1α-cyclopentane acetic acid-γ-lactone. The mass spectrum shows peaks at 488/490, 393/395, 287, 122 and 105.

Alternatively, the analogous alkoxy derivatives can be prepared by reaction with silver oxide and alkyl halide at reflux, for from 1 to 24 hours.

EXAMPLE 13

Using the procedures of example 10, the following 3α-benzoxy-5α-hydroxy-2β-[2-bromo-3(S)-hydroxy-1-trans-alkenyl]-1α-cyclopentane acetic acid-γ-lactones as well as the corresponding 3(R) epimers and the 3α-p-phenylbenzoxy and 3α-acetoxy derivatives, were prepared. The alkenyl groups in these compounds were:
5(2')furanylpentenyl;
4(S)-methyl-5(2')furanylpentenyl;
4(R)-methyl-5(2')-furanylpentenyl;
4(S,R)-methyl-5(2')-furanylpentenyl;
5(3')-furanylpentenyl;
4(S,R)-methyl-5(3')-furanylpentenyl;
4,4-dimethyl-5(2')-furanylpentenyl;
4,4-dimethyl-5(3')-furanylpentenyl;
5-(cyclopent-2'-enyl)-pentenyl;
5-(cyclopent-1'-enyl)-pentenyl;
4(S,R)-methyl-(5-cyclopent-2'-enyl)-pentenyl;
4,4-dimethyl-(5-cyclopent-2'-enyl)-pentenyl;
4,4-dimethyl-(5-cyclopent-1'-enyl)-pentenyl;
4(S)-methyl-5-(cyclopent-2'-enyl)-pentenyl;
5-(3'-methyl-2'-furanyl)-pentenyl;
5-(5'-methyl-2'-furanyl)-pentenyl;
5-(2',5'-dimethyl-3'-furanyl)-pentenyl;
5-(4'-methoxy-2'-furanyl)-pentenyl;
5-(5'-phenoxy-2'-furanyl)-pentenyl;
4-(4-phenyl-cyclohexyl)-pentenyl;
5-(2')-thienyl-pentenyl;
4(S)-methyl-4(2')-furanylbutenyl;
4,4-dimethyl-4(2')-furanylbutenyl.

According to the procedure of example 12, the analogous 3(S) and 3(R) alkoxy derivatives were prepared from the above compounds.

EXAMPLE 14

Using the procedures reported in example 11, the 3(R) and 3(S) epimers of the 3α-benzoxy-5α-hydroxy-2β-[2-bromo-3(S)-hydroxy-1-trans-alkenyl]-1α-cyclopentane acetic acid-γ-lactones listed below were prepared, as well as their 3α-p-phenylbenzoxy, 3α-acetoxy and 2-chloro derivatives:
3-methyl-5(2')-furanylpentenyl;
3-vinyl-5(2')-furanylpentenyl;
3-ethynyl-5(2')-furanylpentenyl;
3-methyl-5(3')-furanylpentenyl;

3-methyl-4(S)-methyl-5(3')-furanylpentenyl;
3-methyl-4(S,R)-methyl-5(2')-furanylpentenyl;
3-methyl-4,4-dimethyl-5(2')-furanylpentenyl;
3-methyl-5-(cyclopent-2'-enyl)-pentenyl;
3-methyl-5-(3'-methyl-2'-furanyl)-pentenyl;
3-methyl-5-(5'-methyl-2'-furanyl)-pentenyl;
3-methyl-5-(2',5'-dimethyl-3'-furanyl)-pentenyl;
3-methyl-5-(4'-methoxy-2'-furanyl)-pentenyl;
3-methyl-5-(5'-phenoxy-2'-furanyl)-pentenyl;
3-methyl-4-(4'-phenyl-cyclohexyl)-butenyl;
3-methyl-5(2')-thienyl pentenyl;
3-methyl-4(S)methyl-4(2')-furanylbutenyl;
3-methyl-4,4-dimethyl-4(2')-furanylbutenyl;
3-methyl-5(2')-norbornylpentenyl;
3-methyl-5(1')-adamantylpentenyl;
3-methyl-5(2')-bicyclo 2,2,2 octylpentenyl;
3-methyl-5-cyclohexylpentenyl;
3-methyl-5-(4'-tert-butylcyclohexyl)-pentenyl;
3-methyl-5-cyclopentylpentenyl;
3-methyl-5-cycloheptylpentenyl;
3-ethyl-5-cyclopropylpentenyl.

From these, according to example 12, the analogous 3(S) and 3(R) methoxy and alkoxy derivatives were prepared.

EXAMPLE 15

(A) 5 ml of 20% aqueous $K_2CO_3$ are added to a solution of 450 mg of 3α-benzoxy-5α-hydroxy-2β-[2-bromo-3(S)-hydroxy-5(2')furanylpent-1-trans-enyl]-1α-cyclopentane acetic acid-γ-lactone in 10 ml of methanol; the resulting mixture is stirred at room temperature for 12 hours until solvolysis is complete and then neutralized with 2N $H_2SO_4$. Extraction with ethyl acetate and evaporation under reduced pressure afford a residue which, after chromatography on silica gel with 1:1 benzene:ethyl ether as eluent, gives 300 mg of 3α,5α-dihydroxy-2β-[2-bromo-3(S)-hydroxy-5(2')furanylpent-1-trans-enyl]-1α-cyclopentane acetic acid-γ-lactone-3,3(S)-bis-THP-ether (oil).

(B) 0.12 ml of dihydropyran and 1 mg of p-toluenesulfonic acid are added to a solution of 200 mg of 3α,5α-dihydroxy-2β-[2-bromo-3(S)-hydroxy-5(2')furanylpent-1-trans-enyl]-1α-cyclopentane acetic acid-γ-lactone-3,3(S)-bis-THP-ether in 5 ml of methylene chloride. After 30 minutes, the reaction is complete and the solution is washed with water, dried over $Na_2SO_4$ and evaporated to dryness to give 290 mg of 3α,5α-dihydroxy-2β-[2-bromo-3(S)-hydroxy-5(2')-furanylpent-1-trans-enyl]-1α-cyclopentane acetic acid-γ-lactone-3α,3(S)-bis-THP-ether (oil).

(C) 2 ml of a 0.5M solution of DIBA are added to a solution of 350 mg of 3α,5α-dihydroxy-2β-[2-bromo-3(S)-hydroxy-5(2')-furanylpent-trans-1-enyl]-1α-cyclopentane acetic acid-γ-lactone-3α,3(S)-bis-THP-ether in 3 ml of toluene, under a nitrogen atmosphere with cooling to −70° C. After 30 minutes of stirring at −70° C., the reaction mixture is treated with a 2N toluene solution of iso-propanol. The cooling bath is removed after 10 minutes and the temperature is allowed to rise to 0° C., when 0.5 ml of water, 1 g of celite and 1 g of anhydrous sodium sulfate are added. Filtration and evaporation to dryness give 352 mg of 3α,5α-dihydroxy-2β-[2-bromo-3(S)-hydroxy-5(2')furanylpent-trans-1-enyl]-1α-cyclopentane acetaldehyde-γ-lactol-bis-THP-ether (oil).

Following the procedures described in example 15, the γ-lactones prepared according to examples 10, 11, 12 13 and 14 afford the following 3α,5α-dihydroxy-2β-[2-bromo-3(S)-hydroxy-1-trans]-1α-cyclopentaneacetaldehyde-γ-lactols, bis-THP-ethers:

5(2')-furanylpentenyl;
4(S)-methyl-5(2')-furanylpentenyl;
4(R)-methyl-5(2')-furanylpentenyl;
4(S,R)-methyl-5(2')-furanylpentenyl;
5(3')-furanylpentenyl;
4(S)-methyl-5(3')-furanylpentenyl;
4(R)-methyl-5(3')-furanylpentenyl;
4(S,R)-methyl-5(3')-furanylpentenyl;
4,4-dimethyl-5(2')-furanylpentenyl;
4,4-dimethyl-5(3')-furanylpentenyl;
5-cyclopent-2'-enyl)pentenyl;
5-(cyclopent-2'-enyl)-pentenyl;
4(S,4-methyl-(5-cyclopent-2'-enyl)-pentenyl;
4,4-dimethyl-(5-cyclopent-2'-enyl)-pentenyl;
4,4-dimethyl-(5-cyclopent-2'-enyl)-pentenyl;
4(S)-methyl-(5-cyclopent-2'-enyl)-pentenyl;
4(R)-methyl-5-(cyclopent-2'-enyl)-pentenyl;
5-(3'-methyl-2'-furanyl)pentenyl;
5-(5'-methyl-2'-furanyl)pentenyl;
5-(2',5'-dimethyl-3'-furanyl)pentenyl;
5-(4'-methoxy-2'-furanyl)pentenyl;
5-(5'-phenoxy-2'-furanyl)pentenyl;
4-(4'-phenylcyclohexyl)pentenyl;
5(2')-thienylpentenyl;
4(S)-methyl-4(2')furanylpentenyl;
4,4-dimethyl-4(2')-furanylpentenyl;
3-methyl-5(2')-furanylpentenyl;
3-vinyl-5(2')-furanylpentenyl;
3-ethynyl-5(2')-furanylpentenyl;
3-methyl-5(3')-furanylpentenyl;
3-vinyl-5(3')-furanylpentenyl;
3-ethynyl-5(3')-furanylpentenyl;
3-methyl-4(S)-methyl-5(3')-furanylpentenyl;
3-vinyl-4(S)-methyl-5(3')-furanylpentenyl;
3-ethynyl-4(S)-methyl-5(3')-furanylpentenyl;
3-methyl-4(S,R)-methyl-5(2')-furanylpentenyl;
3-methyl-4(S,R)-methyl-5(3')-furanylpentenyl;
3-vinyl-4(S,R)-methyl-5(3')-furanylpentenyl;
3-vinyl-4(S,R)-methyl-5(2')-furanylpentenyl;
3-ethynyl-4(S,R)-methyl-5(2')-furanylpentenyl;
3-methyl-4,4-dimethyl-5(2')-furanylpentenyl;
3-methyl-4,4-dimethyl-5(3')-furanylpentenyl;
3-methyl-5-(cyclopent-2'-enyl)-pentenyl;
3-vinyl-5-(cyclopent-2'-enyl)-pentenyl;
3-ethynyl-5-(cyclopent-2'-enyl)-pentenyl;
3-vinyl-5-(cyclopent-2'-enyl)-pentenyl;
3-ethynyl-5-(cyclopent-2'-enyl)-pentenyl;
3-methyl-5-(3'-methyl-2'-furanyl)pentenyl;
3-vinyl-5-(3'-methyl-2'-furanyl)-pentenyl;
3-ethynyl-5-(3'-methyl-2'-furanyl)-pentenyl;
3-methyl-5-(5'-methyl-2'-furanyl)-pentenyl;
3-vinyl-5-(5'-methyl-2'-furanyl)-pentenyl;
3-ethynyl-5-(5'-methyl-2'-furanyl)-pentenyl;
3-methyl-5-(2',5'-dimethyl-3'-furanyl)-pentenyl;
3-vinyl-5-(2',5'-dimethyl-3'-furanyl)-pentenyl;
3-ethynyl-5-(2',5''-dimethyl-3'-furanyl)-pentenyl;
3-methyl-5-(4'-methoxy-2'-furanyl)-pentenyl;
3-methyl-5-(5'-phenoxy-2'-furanyl)-pentenyl;
3-vinyl-5-(5'-phenoxy-2'-furanyl)-pentenyl;
3-ethynyl-5-(5'-phenoxy-2'-furanyl)-pentenyl;
3-vinyl-5-(4'-methoxy-2'-furanyl)-pentenyl;
3-ethynyl-5-(4'-methoxy-2'-furanyl)-pentenyl;
3-methyl-5-(4'-phenylcyclohexyl)-pentenyl;
3-vinyl-4-(4'-phenylcyclohexyl)-pentenyl;
3-ethynyl-4-(4'-phenylcyclohexyl)-pentenyl;
3-methyl-5(2')-thienylpentenyl;

3-vinyl-5(2')-thienyl-pentenyl;
3-ethynyl-5(2')-thienyl-pentenyl;
3-methyl-4(S)-methyl-4(2')-furanyl-butenyl;
3-vinyl-4(S)-methyl-4(2')-furanyl-butenyl;
3-ethynyl-4(S)-methyl-4(2')-furanyl-butenyl;
3,4,4-trimethyl-4(2')-furanyl-butenyl;
3-vinyl-4,4-dimethyl-4(2')-furanyl-butenyl;
3-ethynyl-4,4-dimethyl-4(2')-furanyl-butenyl;
3,4,4-trimethyl-4(3')-furanyl-butenyl;
3-vinyl-4,4-dimethyl-4(3')-furanyl-butenyl;
3-ethynyl-4,4-dimethyl-4(3')-furanyl-butenyl;
3-methyl-5(2')-norbornyl-pentenyl;
3-vinyl-5(2')-norbornyl-pentenyl;
3-ethynyl-5(2')-norbornyl-pentenyl;
3-methyl-5(1')-adamantyl-pentenyl;
3-vinyl-5(1)-adamantyl-pentenyl;
3-ethynyl-5(1)-adamantyl-pentenyl;
3-methyl-5(2')-bicyclo[2,2,2]octyl-pentenyl;
3-vinyl-5(2')-bicyclo[2,2,2]octyl-pentenyl;
3-ethynyl-5(2')-bicyclo[2,2,2]octyl-pentenyl;
3-methyl-5-cyclohexyl-pentenyl;
3-vinyl-5-cyclohexyl-pentenyl;
3-ethynyl-5-cyclohexyl-pentenyl;
3-methyl-5-(4'-tert-butylcyclohexyl)-pentenyl;
3-vinyl-5-(4'-tert-butylcyclohexyl)-pentenyl;
3-ethynyl-5-(4'-tert-butylcyclohexyl)-pentenyl;
3-methyl-5-cyclopentyl-pentenyl;
3-vinyl-5-cyclopentyl-pentenyl;
3-ethynyl-5-cyclopentyl-pentenyl;
3-methyl-5-cycloheptyl-pentenyl;
3-vinyl-5-cycloheptyl-pentenyl;
3-ethynyl-5-cycloheptyl-pentenyl;
3-methyl-5-cyclopropyl-pentenyl;
3-vinyl-5-cyclopropyl-pentenyl;
3-ethynyl-5-cyclopropyl-pentenyl;
as well as the epimeric 3(R), 3-alkoxy, and 2-chloro derivatives.

EXAMPLE 16

A suspension of 922 mg of sodium hydride (80% mineral oil dispersion) in 25 ml of DMSO is stirred at 70° C., under nitrogen, for 4 hours. 4.73 g of triphenylphosphonium pentanoic acid bromide in 6 ml of DMSO is then added, followed by 1.38 g of 3α,5α-dihydroxy-2β-[2-bromo-3(S)-hydroxy-5(2')-furanyl-pent-trans-1-enyl]-1α-cyclopentane acetaldehyde-γ-lactol-bis-THP ether in 2 ml of 1:1 benzene:DMSO. The reaction is complete in 2 hours; water is then added. The resulting mixture is extracted with 1:1 ethyl ether:pentane, and the separated organic phase is washed with 0.5N K$_2$CO$_3$. The basic aqueous extract is acidified with 4N H$_2$SO$_4$ and extracted with 1:1 ethyl ether:pentane. Washing until neutral, drying and solvent removal give 1.32 g of 9α,11α,15(S)-trihydroxy-18,19,20-trinor-17(2')-furanyl-prost-cis-5-en-13-inoic acid-11,15-bis-THP-ether (oil).

To a solution of this product in 5 ml of ethyl ether, excess diazomethane (ether solution) is added dropwise. After several minutes, the reaction is quenched with acetic acid, and the solution is washed with bicarbonate solution and water. Drying and solvent removal under vacuum afford a residue which is chromatographed on SiO$_2$ (1:1 benzene:ethyl ether as eluent) to give 1.80 g of 9α,11α,15(S)-trihydroxy-18,19,20-trinor-17(2')-furanyl-prost-cis-5-en-13-inoic acid methyl ester-11,15-bis-THP ether (oil).

Starting from the lactols prepared as in example 15, the procedure gave the analogous prostaglandin derivatives reported in the preceding examples, plus their corresponding 15-epi analogues.

EXAMPLE 17

(A) 5 ml of 0.5N oxalic acid is added to a solution of 550 mg of 9α,11α,15(S)-trihydroxy-18,19,20-trinor-17(2')-furanyl-prost-cis-5-en-13-inoic acid methyl ester-11,15-bis-THP ether in 10 ml of methanol. The mixture is stirred at 50° C. for two hours. Evaporation of the methanol, extraction with ethyl ether, drying and solvent removal give a residue which is chromatographed on SiO$_2$ (with 80:20 cyclohexane:ethyl acetate as eluent) to afford 350 mg of 9α,11α,15(S)-trihydroxy-18,19,20-trinor-17(2')-furanyl-prost-cis-5-en-13-inoic acid methyl ester ([α$_D$]= +27 in CHCl$_3$) (18,19,20-trinor-17(2')-furanyl-13,14-didehydro PGF$_2$ methyl ester). The mass spectrum shows peaks at 390, 372, 354, 341, 323, 291, 273, 231,81.

(B) Alternatively, the pyranyl group may be removed by treating 110 mg in 5 ml of methanol with 0.1 ml of water and 5 mg of Amberlyst 15 resin. After stirring at 20° C. for 12 hours, the methanol is evaporated. The resulting mixture is extracted with ethyl ether, washed with NaHCO$_3$ and evaporated to dryness. TLC chromatography of the residue on SiO$_2$ (with 3:1 ethyl acetate:benzene) affords 75 mg of the product 9α,11α,15(S)-trihydroxy-18,19,20-trinor-17(2')-furanyl-prost-cis-5-en-13-inoic acid methyl ester.

EXAMPLE 18

0.8 ml of Jones reagent is added dropwise to a solution of 0.35 g of 9α,11α,15(S)-trihydroxy-18,19,20-trinor-18,19,20-trinor-17(2')-furanyl-prost-cis-5-en-13-inoic acid methyl ester-11,15-bis-THP-ether in 15 ml of acetone, with cooling to −15° C. After the addition the temperature is allowed to rise to −8° C. and the mixture is stirred for 20 minutes. It is then diluted with benzene, washed with saturated (NH$_4$)$_2$SO$_4$ solution until neutral, dried and evaporated at 20° C. under vacuum. The 0.345 g residue is dissolved in 15 ml of acetone and treated with 8 ml of 0.5N oxalic acid at 40° C. for 8 hours. After the acetone is evaporated to give a residue which, upon chromatography on SiO$_2$ (with 80:20 methylene chloride:ethyl acetate) affords 0.235 g of 9-oxo-11α,15(S)-dihydroxy-18,19,20-trinor-16(S)-methyl-17(2')-furanyl-prost-cis-5-en-13-inoic acid methyl ester ([α$_D$]= −37 in CHCl$_3$) (18,19,20-trinor-16(S)-methyl-17(2')-furanyl-13,14-didehydro-PGE$_2$-methyl ester). The mass spectrum shows peaks at 402, 384, 366, and 257.

EXAMPLE 19

A solution of 0.27 g of 9-oxo-11α,15(S)-dihydroxy-18,19,20-trinor-16(S)-methyl-17(2')-furanyl-prost-5,10-dien-13-ionic acid methyl ester-bis-THF-ether in 35 ml of acetone and 40 ml of 0.2N oxalic acid is refluxed for 6 hours. The acetone is then removed under vacuum and the aqueous residue is extracted with ethyl ether. Washing the extract with water, drying and evaporation to dryness afford, after TLC with 1:1 cyclohexane:ethyl ether, 0.13 g of 9-oxo-15(S)-hydroxy-18,19,20-trinor-16(S)-methyl-17(2')-furanyl-prost-5,10-dien-13-inoic acid methyl ester (18,19,20-trinor-16(S)-methyl-17(2')-furanyl-13,14-didehydro-PGA$_2$ methyl ester). The mass spectrum shows peaks at 384, 366, 308, 257.

EXAMPLE 20

The following 13,14-didehydro-PGF$_{2\alpha}$, PGE$_2$ and PGA$_2$ methyl esters and 15-methoxy derivatives were prepared using the procedures described in examples 17,18, and 19, starting from the 9,11,15(S)-trihydroxy-prost-cis-5-en-13-inoic acid methyl esters-11,15-bis-THF-ethers prepared according to example 16:

18,19,20-trinor-17(3')-furanyl;
18,19,20-trinor-16(S)-methyl-17(2')-furanyl;
18,19,20-trinor-16(R)-methyl-17(2')-furanyl;
18,19,20-trinor-16(S,R)-methyl-17(2')-furanyl;
18,19,20-trinor-16,16-dimethyl-17(2')-furanyl;
18,19,20-trinor-16,16-dimethyl-17(3')-furanyl;
18,19,20-trinor-17-cyclopent-2'-enyl;
18,19,20-trinor-17-cyclopent-1'-enyl;
18,19,20-trinor-16(S,R)-methyl-17-cyclopent-2'-enyl;
18,19,20-trinor-16,16-dimethyl-17-cyclopent-2'-enyl;
18,19,20-trinor-16,16-dimethyl-17-cyclopent-1'-enyl;
18,19,20-trinor-16(S)-methyl-17-cyclopent-2'-enyl;
18,19,20-trinor-16(S,R)-methyl-17-cyclopent-2'-enyl;
18,19,20-trinor-17-(3'-methyl)-(2')-furanyl;
18,19,20-trinor-17-(5'-methyl)-(2')-furanyl;
18,19,20-trinor-17-(2',5'-dimethyl)-(3')-furanyl;
18,19,20-trinor-17-(4'-methoxy)-(2')-furanyl;
18,19,20-trinor-17-(5'-phenoxy)-(2')-furanyl;
17,18,19,20-tetranor-16-phenyl-16-cyclohexyl;
18,19,20-trinor-17-thienyl;
17,18,19,20-tetranor-16(S)-methyl-16(2')-furanyl;
17,18,19,20-tetranor-16(S)-methyl-16(3')-furanyl;
17,18,19,20-tetranor-16,16-dimethyl-16(2')-furanyl;
17,18,19,20-tetranor-16,16-dimethyl-16(3')-furanyl;
19,20-dinor-18(2')-furanyl;
19,20-dinor-18(3')-furanyl;
19,20-dinor-16(S)-methyl-18(2')-furanyl;
19,20-dinor-16(S)-methyl-18(3')-furanyl;
18,19,20-trinor-15-methyl-18(2')-furanyl;
18,19,20-trinor-15-vinyl-17(2')-furanyl;
18,19,20-trinor-15-ethynyl-17(2')-furanyl;
18,19,20-trinor-15-ethynyl-17(2')-furanyl;
18,19,20-trinor-15,16(S)-dimethyl-17(2')-furanyl;
18,19,20-trinor-15,16(S)-dimethyl-17(3')-furanyl;
18,19,20-trinor-15,16(S,R)-dimethyl-17(2')-furanyl;
18,19,20-trinor-15,16(S,R)-dimethyl-17(3')-furanyl;
18,19,20-trinor-15-methyl-17-cyclopent-2'-enyl;
18,19,20-trinor-15-methyl-17-cyclopent-3'-enyl;
18,19,20-trinor-15-methyl-17-(3'-methyl-2')-furanyl;
18,19,20-trinor-15-methyl-17-(5'-methyl-2')-furanyl;
18,19,20-trinor-15-methyl-17-(2',5'-dimethyl-3')-furanyl;
18,19,20-trinor-15-methyl-17-(4'-methoxy-2')-furanyl;
18,19,20-trinor-15-methyl-17-(5'-phenoxy-2')-furanyl;
18,19,20-trinor-15-methyl-17(2')-thienyl;
18,19,20-trinor-15-methyl-17(2')-norbornyl;
18,19,20-trinor-15-methyl-17(1')-adamantyl;
18,19,20-trinor-15-methyl-17(2')-bicyclo[2,2,2]octyl;
18,19,20-trinor-15-methyl-17-cyclohexyl;
18,19,20-trinor-15-methyl-17-(4'-tert-butyl)-cyclohexyl;
18,19,20-trinor-15-methyl-17-cyclopentyl;
18,19,20-trinor-15-methyl-17-cycloheptyl;
18,19,20-trinor-15-methyl-17-cyclopropyl;
17,18,19,20-tetranor-15,16-dimethyl-16-(4'-phenyl)-cyclohexyl;
17,18,19,20-tetranor-15,16-dimethyl-16(2')-furanyl;
17,18,19,20-tetranor-15,16,16-trimethyl-16(2')-furanyl;
17,18,19,20-tetranor-15,16-dimethyl-16(3')-furanyl;
17,18,19,20-tetranor-15,16,16-trimethyl-16(3')-furanyl;

as well as the analogous 15-epi derivatives.

EXAMPLE 21

100 mg of lithium hydroxide is added to a solution of 635 mg of 9$\alpha$,11$\alpha$,15(S)-trihydroxy-18,19,20-trinor-17(2')-furanyl-prost-cis-5-en-13-inoic acid in 7 ml of methanol and 1.6 ml of water; the resulting mixture is stirred at 25° C. for 5 hours. 15 ml of water is then added, the methanol is evaporated under vacuum, and the solution is extracted with ethyl ether. The aqueous phase is acidified with a saturated solution of monobasic phosphate and extracted several times with ethyl ether. After drying, the ether extract is concentrated under vacuum to give 595 mg of 9$\alpha$,11$\alpha$,15(S)-trihydroxy-18,19,20-trinor-17(2')-furanyl-prost-cis-5-en-13-inoic acid, ([$\alpha$]$_D$ = +31°; CHCl$_3$).

Using this procedure, the 13,14-didehydro-PGF$_{2\alpha}$ methyl esters described in example 20 were saponified to give the corresponding 13,14-didehydro-PGF$_{2\alpha}$ and 13,14-didehydro-15-epi-PGF$_{2\alpha}$ derivatives.

We claim:

1. Compounds having the following formula (I)

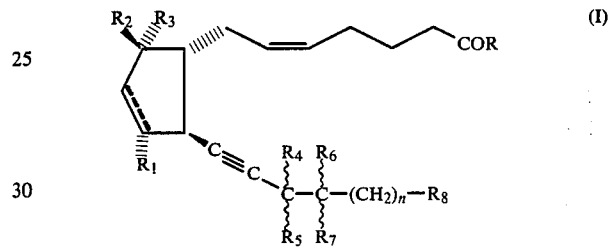

where R is OH; C$_1$–C$_{12}$ alkoxy with optional substitution by one or more phenyl groups, said phenyl groups being optionally substituted by C$_1$–C$_6$ alkyl or halo-C$_1$–C$_6$ alkyl, or heterocyclic radicals chosen from pyridyl, pyrazolyl and pyrazolinyl; or a

group where R' and R" are, independently of one another, hydrogen, C$_1$–C$_6$ alkyl, phenyl or heterocyclic, or a heterocyclic radical formed by R', R" and the nitrogen wherein the heterocyclic or heterocyclic radical is chosen from pyridyl, pyrazolyl or pyrazolinyl; the symbol $\equiv\!\!\equiv\!\!\equiv$ represents a single or double bond, where, when $\equiv\!\!\equiv\!\!\equiv$ is a double bond, R$_1$ is hydrogen and R$_2$ and R$_3$, taken together, form an oxo group, and when $\equiv\!\!\equiv\!\!\equiv$ is a single bond, R$_1$ is hydroxy, R$_2$ is hydrogen and R$_3$ is either hydroxy, C$_2$–C$_6$ alkanoyloxy or benzoyloxy, or forms with R$_2$ an oxo group; one of R$_4$ and R$_5$ is hydroxy or C$_1$–C$_6$ alkoxy and the other is hydrogen, C$_1$–C$_4$ alkyl, phenyl, C$_2$–C$_4$ alkenyl or C$_2$–C$_4$-alkynyl; R$_6$ and R$_7$ are, independently of one another, hydrogen, C$_1$–C$_4$ alkyl, fluoro, phenyl or phenyl substituted by methyl, chloro, fluoro or trifluoromethyl; n is zero, 1, 2 or 3; R$_8$ is furyl unsubstituted or substituted with one or more substituents chosen from a group consisting of (a') halogen, (b') trihalo-C$_1$–C$_6$-alkyl, (c') C$_1$–C$_4$ alkyl, (d') C$_1$–C$_4$ alkoxy, (e') phenyl and (f') phenoxy, and pharmaceutically or veterinarily acceptable salts thereof.

2. A compound of formula (I) according to claim 1 wherein R$_8$ is unsubstituted furyl.

3. A compound of the following formula (I)

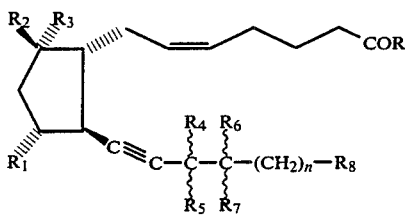 (I)

where R is OH; a $C_1$–$C_{12}$ alkoxy group; or a

group wherein R' and R" are, independently of one another, hydrogen or $C_1$–$C_6$ alkyl; $R_1$ is hydroxy; $R_2$ is hydrogen and $R_3$ is hydroxy, or $R_2$ and $R_3$, taken together, form an oxo group; one of $R_4$ and $R_5$ is hydrogen and the other is hydroxy; $R_6$ and $R_7$ are, independently of one another, hydrogen, $C_1$–$C_4$ alkyl or fluoro; n is zero or an integer of 1 to 3; and $R_8$ is furyl, and the pharmaceutically or veterinarily acceptable salts thereof.

4. The compound 9-oxo-11α,15(S)-dihydroxy-18,19,20-trinor-16(S)-methyl-17-(2'-furanyl)-prost-cis-5-en-13-ynoic acid and the $C_1$–$C_6$ alkyl esters, the unsubstituted carboxamide and the pharmaceutically or veterinarily acceptable salts thereof.

5. The compound 9-oxo-11α,15(S)-dihydroxy-18,19,20-trinor-16(S)-methyl-17-(2'-furanyl)-prost-cis-5-en-13-ynoic acid methyl ester.

6. The compound 9-oxo-11α,15(S)-dihydroxy-18,19,20-trinor-17-(2'-furanyl)-prost-cis-5-en-13-ynoic acid and the $C_1$–$C_6$ alkyl esters, the unsubstituted carboxamide and the pharmaceutically or veterinarily acceptable salts thereof.

7. An alkyl ester according to claim 6 wherein the alkyl ester is the methyl ester.

8. A compound selected from the group consisting of:
9α,11α,15(S)-trihydroxy-18,19,20-trinor-17(2')-furanyl-prost-cis-5-en-13-ynoic acid;
9α,11α,15(S)-trihydroxy-18,19,20-trinor-17(3')-furanyl-prost-cis-5-en-13-ynoic acid;
9α,11α,15(S)-trihydroxy-18,19,20-trinor-16(S)-methyl-17(2')-furanyl-prost-cis-5-en-13-ynoic acid;
9α,11α,15(S)-trihydroxy-18,19,20-trinor-16(R)-methyl-17(2')-furanyl-prost-cis-5-en-13-ynoic acid;
9α,11α,15(S)-trihydroxy-18,19,20-trinor-16(S,R)-methyl-17(2')-furanyl-prost-cis-5-en-13-ynoic acid;
9α,11α,15(S)-trihydroxy-18,19,20-trinor-16-fluoro-17(2')-furanyl-prost-cis-5-en-13-ynoic acid;
9α,11α,15(S)-trihydroxy-18,19,20-trinor-16,16-dimethyl-17(2')-furanyl-prost-cis-5-en-13-ynoic acid;
9α,11α,15(S)-trihydroxy-18,19,20-trinor-16(S)-methyl-17(3')-furanyl-prost-cis-5-en-13-ynoic acid;
9α,11α,15(S)-trihydroxy-18,19,20-trinor-16(R)-methyl-17(3')-furanyl-prost-cis-5-en-13-ynoic acid;
9α,11α,15(S)-trihydroxy-18,19,20-trinor-16(S,R)-methyl-17(3')-furanyl-prost-cis-5-en-13-ynoic acid;
9α,11α,15(S)-trihydroxy-18,19,20-trinor-16-fluoro-17(3')-furanyl-prost-cis-5-en-13-ynoic acid;
9α,11α,15(S)-trihydroxy-18,19,20-trinor-16,16-dimethyl-17(3')-furanyl-prost-cis-5-en-13-ynoic acid;
9-oxo-11α,15(S)-dihydroxy-18,19,20-trinor-17(3')-furanyl-prost-cis-5-en-13-ynoic acid;
9-oxo-11α,15(S)-dihydroxy-18,19,20-trinor-16(R)-methyl-17(2')furanyl-prost-cis-5-en-13-ynoic acid;
9-oxo-11α,15(S)-dihydroxy-18,19,20-trinor-16(S,R)-methyl-17(2')furanyl-prost-cis-5-en-13-ynoic acid;
9-oxo-11α,15(S)-dihydroxy-18,19,20-trinor-16-fluoro-17(2')furanyl-prost-cis-5-en-13-ynoic acid;
9-oxo-11α,15(S)-dihydroxy-18,19,20-trinor-16,16-dimethyl-17(2')-furanyl-prost-cis-5-en-13-ynoic acid;
9-oxo-11α,15(S)-dihydroxy-18,19,20-trinor-16(S)-methyl-17(3')furanyl-prost-cis-5-en-13-ynoic acid;
9-oxo-11α,15(S)-dihydroxy-18,19,20-trinor-16(R)-methyl-17(3')-furanyl-prost-cis-5-en-13-ynoic acid;
9-oxo-11α,15(S)-dihydroxy-18,19,20-trinor-16(S,R)-methyl-17(3')-furanyl-prost-cis-5-en-13-ynoic acid;
9-oxo-11α,15(S)-dihydroxy-18,19,20-trinor-16-fluoro-17(3')furanyl-prost-cis-5-en-13-ynoic acid;
9-oxo-11α,15(S)-dihydroxy-18,19,20-trinor-16,16-dimethyl-17(3')-furanyl-prost-cis-5-en-13-ynoic acid,
and the $C_1$–$C_6$ alkyl esters, the unsubstituted carboxy amides and the pharmaceutically or veterinarily acceptable salts thereof.

9. An alkyl ester according to claim 8 wherein the alkyl ester is the methyl ester.

10. A compound selected from the group consisting of:
9α,11α,15(S)-trihydroxy-17,18,19,20-tetranor-16(S)-methyl-16(2')furanyl-prost-cis-5-en-13-ynoic acid;
9α,11α,15(S)-trihydroxy-17,18,19,20-tetranor-16(S)-methyl-16(3')furanyl-prost-cis-5-en-13-ynoic acid;
9α,11α,15(S)-trihydroxy-17,18,19,20-tetranor-16,16-dimethyl-16(2')furanyl-prost-cis-5-en-13-ynoic acid;
9α,11α,15(S)-trihydroxy-17,18,19,20-tetranor-16,16-dimethyl-16(3')furanyl-prost-cis-5-en-13-ynoic acid;
9α,11α,15(S)-trihydroxy-19,20-dinor-18(2')furanyl-prost-cis-5-en-13-ynoic acid;
9α,11α,15(S)-trihydroxy-19,20-dinor-18(3')furanyl-prost-cis-5-en-13-noic acid;
9α,11α,15(S)-trihydroxy-19,20-dinor-16(S)-methyl-18(2')furanyl-prost-cis-5-en-13-ynoic acid;
9α,11α,15(S)-trihydroxy-19,20-dinor-16(S)-methyl-18(3')furanyl-prost-cis-5-en-13-ynoic acid;
9-oxo-11α,16(S)-dihydroxy-17,18,19,20-tetranor-16(S)-methyl-16(2')furanyl-prost-cis-5-en-13-ynoic acid;
9-oxo-11α,15(S)-dihydroxt-17,18,19,20-tetranor-16(S)-methyl-16(3')furanyl-prost-cis-5-en-13-ynoic acid;
9-oxo-11α,15(S)-dihydroxy-17,18,19,20-tetranor-16,16-dimethyl-16(2')furanyl-prost-cis-5-en-13-ynoic acid;
9-oxo-11α,15(S)-dihydroxy-17,18,19,20-tetranor-16,16-dimethyl-16(3')furanyl-prost-cis-5-en-13-ynoic acid;
9-oxo-11α,15(S)-dihydroxy-19,20-dinor-18(2')furanyl-prost-cis-5-en-13-ynoic acid;
9-oxo-11α,15(S)-dihydroxy-19,20-dinor-18(3')-furanyl-prost-cis-5-en-13-ynoic acid;
9-oxo-11α,15(S)-dihydroxy-19,20-dinor-16(S)-methyl-18(2')furanyl-prost-cis-5-en-13-ynoic acid;
9-oxo-11α,15(S)-dihydroxy-19,20-dinor-16(S)-methyl-18(3')furanyl-prost-cis-5-en-13-ynoic acid,
and the $C_1$–$C_6$ alkyl esters, the unsubstituted carboxy amides and the pharmaceutically or veterinarily acceptable salts thereof.

11. An alkyl ester according to claim 10 wherein the alkyl ester is the methyl ester.

12. A pharmaceutical or veterinary composition suitable for use in preventing and treating ulcers, said composition comprising a therapeutically effective amount of a compound according to claim 1 and a pharmaceutically or veterinarily acceptable and/or diluent.

13. A pharmaceutical composition for use in presenting and treating ulcers comprising a therapeutically effective amount of a compound of claim 1 and a pharmaceutically acceptable carrier.

14. A pharmaceutical composition for use in preventing and treating ulcers comprising a therapeutically effective amount of a compound of claim 4 and a pharmaceutically acceptable carrier.

15. A pharmaceutical composition for use in preventing and treating ulcers comprising a therapeutically effective amount of the compound of claim 5 and a pharmaceutically acceptable carrier.

16. Method of inhibiting and preventing ulcers in a patient in need of such treatment, said method comprising administering to said patient an effective amount of a compound of claim 1.

17. Method of inhibiting and preventing ulcers in a patient in need of such treatment, said method comprising administering to said patient an effective amount of a compound of claim 4.

18. Method of inhibiting and preventing ulcers in a patient in need of such treatment, said method comprising administering to said patient an effective amount of the compound of claim 5.

* * * * *